US011185863B2

(12) United States Patent
Irmscher et al.

(10) Patent No.: US 11,185,863 B2
(45) Date of Patent: Nov. 30, 2021

(54) SYSTEM FOR APPLYING A REAGENT TO A SAMPLE

(71) Applicant: KONINKLIJKE PHILIPS N.V., Eindhoven (NL)

(72) Inventors: Matthias Irmscher, Veldhoven (NL); Toon Hendrik Evers, Eindhoven (NL); Stefan Johannes Hendrikus Toonen, North Brabant (NL); Marlieke Joan Overdijk, Helmond (NL); Harma Martine Feitsma, Vught (NL); Thomas Johannes Van Gijsel, Helmond (NL); Wilbert Hendrik Bouwman, Elst (NL); Eveline Catharina Anna Clasina Den Biezen-Timmermans, Dongen (NL); Willem-Jan Arend De Wijs, Oss (NL)

(73) Assignee: Koninklijke Philips N.V., Eindhoven (NL)

( * ) Notice: Subject to any disclaimer, the term of this patent is extended or adjusted under 35 U.S.C. 154(b) by 325 days.

(21) Appl. No.: 16/337,738

(22) PCT Filed: Sep. 29, 2017

(86) PCT No.: PCT/EP2017/074742
§ 371 (c)(1),
(2) Date: Mar. 28, 2019

(87) PCT Pub. No.: WO2018/060405
PCT Pub. Date: Apr. 5, 2018

(65) Prior Publication Data
US 2019/0344263 A1    Nov. 14, 2019

Related U.S. Application Data

(60) Provisional application No. 62/407,099, filed on Oct. 12, 2016.

(30) Foreign Application Priority Data

Sep. 30, 2016   (EP) .................................... 16191648

(51) Int. Cl.
*B01L 3/00*         (2006.01)
*F04B 7/04*         (2006.01)
(Continued)

(52) U.S. Cl.
CPC ............. *B01L 3/5029* (2013.01); *B01L 3/523* (2013.01); *F04B 7/04* (2013.01); *F04B 13/00* (2013.01);
(Continued)

(58) Field of Classification Search
CPC .. B01L 3/502; B01L 3/523; B01L 2200/0605; B01L 2200/0647;
(Continued)

(56) References Cited

U.S. PATENT DOCUMENTS 5,658,531 A    8/1997  Cope
6,027,945 A    2/2000  Smith
(Continued)

FOREIGN PATENT DOCUMENTS

CA    2664449 A1 *  4/2008  ........ B01L 3/502715
EP    1319716 B1    7/2013
(Continued)

OTHER PUBLICATIONS

Yang, Fang "Electrokinetic Mixing and Separation in Microfluidic Systems", Theses and Dissertation, 2013.

*Primary Examiner* — Jennifer Wecker
*Assistant Examiner* — Kathryn Elizabeth Limbaugh

(57) ABSTRACT

In order to provide a system allowing an improved and facilitated preparation of a sample for an appropriate analysis, a device for preparing a patient's sample before analysis
(Continued)

is provided. The device comprises a housing (10, 30) and an actuator (50). The housing includes a receiving chamber (32). The receiving chamber is configured for receiving a liquid. The actuator is movable relative to the housing. The actuator is configured for extracting a predetermined amount of the liquid received in the receiving chamber and for supplying the extracted liquid to a reagent chamber, so that the reagent is suspended in the liquid. The actuator comprises a metering chamber (52) configured for receiving the predetermined amount of the liquid and for supplying the predetermined amount of the liquid to the reagent chamber.

21 Claims, 13 Drawing Sheets

(51) Int. Cl.
*F04B 13/00* (2006.01)
*A61B 10/00* (2006.01)
*F04B 19/00* (2006.01)

(52) U.S. Cl.
CPC ... *A61B 10/0045* (2013.01); *B01L 2200/0605* (2013.01); *B01L 2200/0647* (2013.01); *B01L 2200/16* (2013.01); *B01L 2300/0672* (2013.01); *B01L 2300/0681* (2013.01); *B01L 2300/087* (2013.01); *B01L 2400/049* (2013.01); *B01L 2400/0478* (2013.01); *B01L 2400/0481* (2013.01); *B01L 2400/065* (2013.01); *F04B 19/006* (2013.01)

(58) Field of Classification Search
CPC ......... B01L 2200/16; B01L 2300/0672; B01L 2300/0681; B01L 2300/087; B01L 2400/0478; B01L 2400/0481; B01L 2400/049; B01L 2400/065; F04B 7/04; F04B 19/006; A61B 10/0045
See application file for complete search history.

(56) References Cited

U.S. PATENT DOCUMENTS

| | | |
|---|---|---|
| 6,787,307 B1 | 9/2004 | Bitner |
| 6,969,603 B2 | 11/2005 | Carninci |
| 8,937,174 B2 | 1/2015 | Himmelreich |
| 2004/0152076 A1 | 8/2004 | Murphy |
| 2006/0029517 A1 | 2/2006 | Hartselle |
| 2007/0183935 A1 | 8/2007 | Battrell |
| 2008/0226510 A1 | 9/2008 | Peuker |
| 2010/0002535 A1 | 1/2010 | Cho |
| 2013/0045501 A1 | 2/2013 | Hu |
| 2013/0071944 A1 | 3/2013 | Ulrich |
| 2013/0273548 A1 | 10/2013 | Baloch |
| 2015/0076008 A1* | 3/2015 | Athanasiou ......... B01L 3/50851 205/792 |
| 2015/0099291 A1 | 4/2015 | Ririe |
| 2016/0033375 A1 | 2/2016 | Huang |
| 2016/0051935 A1 | 2/2016 | Didar |

FOREIGN PATENT DOCUMENTS

| | | |
|---|---|---|
| JP | 04214255 B2 | 1/2009 |
| WO | 2005060658 A1 | 7/2005 |

* cited by examiner

SYSTEM FOR APPLYING A REAGENT TO A SAMPLE

CROSS-REFERENCE TO PRIOR APPLICATIONS

This application is the U.S. National Phase application under 35 U.S.C. § 371 of International Application No. PCT/EP2017/074742, filed on Sep. 29, 2017, which claims the benefit of European Patent Application No. 16191648.1, filed on Sep. 30, 2016 and U.S. Provisional Patent Application Ser. No. 62/407,099, filed Oct. 12, 2016. These applications are hereby incorporated by reference herein.

This invention was made with US Government support under HR0011-12-C-0007 awarded by the Defense Advanced Research Projects Agency. The US Government has certain rights in this invention.

FIELD OF THE INVENTION

The invention generally relates to in-vitro diagnostics, such as for example molecular diagnostics. Particularly, the invention relates to a system for handling and preparing a sample so as to allow such diagnostics.

BACKGROUND OF THE INVENTION

For many diseases, the clinically relevant concentrations of analytes (e.g. nucleic acids, proteins, clinical chemistry elements, or other biomarkers) in a sample are extremely low and as a result cannot be detected directly within an acceptable time frame. To address this problem, patient samples are typically first subjected to processes that purify the targeted analyte and/or increase its concentration. These processes are collectively called sample preparation. Upon sample preparation for molecular diagnostics (i.e. detection of nucleic acids), most commercially available diagnostic methods proceed by amplifying the target in question, thereby further increasing its concentration, often by many orders of magnitude.

A sample preparation process is generally preceded by the sample uptake from the patient. This uptake can be performed directly to a sample application device (e.g. extraction of blood from the vessel by firing or piercing the latter, uptake of tissue) or by using a disposable swab to acquire tissue or liquid samples of for example blood, urinal, sperm, nasal or vaginal secretions. To analyze the swab, the patient material may be rinsed off the swab and then becomes available for downstream processing. Rinsing a swab requires the tip of the swab to be immersed in a liquid under slight agitation. The liquid can have lysis activity.

One of the standard sample preparation processes of molecular diagnostics is the Boom method, combined with magnetic particle-based extraction. In this method, cells and viruses are first lysed at a high ionic strength and acidic pH. Under these buffer conditions, DNA and RNA can bind to the silica coating of the particles and can thus be extracted from solution. The generic protocol for this method typically comprises at least five steps:

Addition of patient sample to lysis buffer.
Mixing of patient sample with lysis buffer.
Removal of either DNA or RNA by filtration (optional).
Addition of magnetic particles to sample.
Mixing of magnetic particles with sample.

Other methods make use of silica filters that capture nucleic acids from the sample liquid as it passes through the filter and release them when a second buffer is flushed through.

In many sample preparation methods, the extraction of analytes is achieved by binding of molecules to a solid support. This can be done by either allowing sample liquid to flow through a porous structure, i.e. a filter, or by suspending suitable particles in a substantially quiescent liquid. In the magneto-capillary valve technology (see e.g. WO 2009/083862), the latter approach is implemented by first binding analytes to magnetic particles before magnetically transporting them through several washing chambers. In other embodiments, magneto-capillary valve by magnetically transporting contaminants, other components or irrelevant portions of lysed cells to a waste chamber, implementing a washing function of the sample.

Usually the sample preparation comprises the step of putting in contact a reactant with the sample, which e.g. specifically binds the analytes with said magnetic particles or chemically and/or mechanically interact with the cells of the sample for lysis purpose.

All these steps of sample preparation require a sample application system comprising different chambers, transportation, mixing, incubation, which can be time-consuming and cumbersome. Furthermore, these steps need usually to be carried out in a laboratory by trained personnel, especially to be sure that all the steps are performed in the right way and reliably. To enable the analytes based analysis of patient samples at the point-of-care, i.e. outside a laboratory, sample preparation methods need to be optimized for high ease-of-use to enable seamless integration into existing workflows and to largely exclude user errors.

SUMMARY OF THE INVENTION

In view of the above-mentioned problems, it can be seen as an object of the invention to provide a system allowing a preparation of sample for an appropriate analysis. This and further objects are solved by the subject-matter of the independent claims. Further embodiments are described in the dependent claims.

According to the invention, a device for preparing a patient's sample before analysis is provided. The device comprises a housing and an actuator. The housing includes a receiving chamber. The receiving chamber is configured for receiving a liquid. The actuator is movable relative to the housing. The actuator is further configured for extracting a predetermined amount of the liquid received in the receiving chamber and for supplying the extracted liquid to a reagent chamber, so that the reagent is suspended in the liquid. Optionally, the actuator comprises a metering chamber configured for receiving the predetermined amount of the liquid and for supplying the predetermined amount of the liquid to the reagent chamber.

In an example, the receiving chamber is configured for receiving the sample and delivering a liquid.

In a further example, the receiving chamber is configured for receiving the liquid including the patient's sample. The receiving chamber may receive also a non-liquid sample. But in all cases, it delivers a liquid (the sample per se or the sample mixed with another reagent, in addition to supplying a reagent further downstream the metering chamber.

The predetermined amount of the liquid is predetermined by providing the metering chamber to be able to accommodate this predetermined volume, i.e. amount of the liquid. The amount of liquid in the metering chamber is equal or minimally greater to the amount of liquid to be extracted, i.e. supplied, to the reagent chamber.

In an example, the received amount of liquid is not necessarily equal to the supplied amount of liquid, i.e. a small part of the liquid in the metering chamber may stay in the metering chamber after the supply to the reagent chamber. Hence, a determined amount is delivered out from the metering chamber. This determined amount can be the predetermined amount or less.

In an example, the housing includes an outflow to the reagent chamber.

The actuator can also be referred to as actuator arrangement.

In an example, it is provided to receive a sample in the receiving chamber and to add a fluid reagent to the receiving chamber to provide the liquid. This is different than a reagent provided downstream the metering chamber.

In an example, it is provided to receive a non-liquid or non-fluid sample in the receiving chamber and to add a fluid reagent to the receiving chamber to provide the liquid.

In another example, it is provided to receive a liquid or fluid sample in the receiving chamber and to add a non-fluid or non-liquid reagent to the receiving chamber to provide the liquid.

In a further example, it is provided to receive a liquid or fluid sample in the receiving chamber and to add a liquid or fluid reagent to the receiving chamber to provide the liquid.

In a still further example, it is provided to receive a liquid or fluid sample in the receiving chamber to the receiving chamber to provide the liquid.

In other examples, a liquid or fluid sample is provided and a liquid or fluid reagent is added downstream the metering chamber.

In further example, a liquid or fluid sample is provided and a non-liquid or non-fluid reagent is added downstream the metering chamber.

The term "reagent chamber" relates to a volume into which the predetermined amount of liquid is supplied. The reagent may be provided to the liquid in that chamber or when flowing towards the chamber. For example, the reagent is provided inside the chamber or after the outflow of the metering chamber. The reagent may also be provided before the metering chamber. In an example, the reagent is provided after the metering chamber. A further reagent may be added before the metering chamber. The reagent is present in the fluid in the reagent chamber.

In an example, the reagent is provided to the liquid in the reagent chamber. The height of this reagent chamber, especially with regards to the thickness of the layer of reagent provided on a side of the reagent chamber, preferably facing an inlet of the reagent chamber, may be provided as key to create a good mixing, for example by turbulence. Furthermore, the inlet of the reagent chamber is provided as key to generate the turbulence. For example, channel(s) having small cross-section with respect to the cross-section of the metering chamber support in creating the turbulence. The inlet is configured to increase the flow of the liquid into the reagent chamber, thus improving the mixing and the turbulence.

The term "reagent reservoir" relates to a volume in which a reagent is provided, which reagent is to be added to the liquid.

In an example, a reagent reservoir is provided configured for receiving the reagent.

In an example, a first reagent reservoir is provided that is configured to receive and/or store the reagent, e.g. a dry reagent.

In an example, the reagent reservoir is also referred to as reagent chamber.

According to an example, the metering chamber has a first opening to draw in the liquid and a second opening, different from the first opening, to eject the liquid.

The first opening is an inlet of the metering chamber and the second opening is an outlet of the metering chamber.

The term "to draw in" refers to the extraction of the liquid from the receiving chamber.

The term "to eject" refers to the provision (supply) of the liquid which has been extracted into the metering the chamber.

According to an example, the device comprises a reagent reservoir comprising the reagent, preferably a dry reagent.

In an example, the reagent reservoir is included in the housing. The actuator is configured for supplying the extracted liquid to the reagent reservoir According to an example, the device further comprises a container with the actuator and the housing including the receiving chamber. The device further comprises a base comprising an internal fluidic path with an inlet. The container and the base are provided as separate parts that are configured to be assembled together during a sample preparation process. The base is configured for interacting engagement with a portion of the container such that the inlet of the base is facing an outlet of the metering chamber. The base is further provided with members arranged to open a path between the actuator and the base once they are functionally engaged with each other. As an option, the base comprises the reagent chamber.

The inlet of the base is also referred to as an inflow, and the outlet of the metering chamber as an outflow.

In the engaging interacting state, the base and the container are functionally connected with each other.

According to an example, the base comprises at least one processing chamber or detecting chamber, into which the liquid is supplied by actuating of the actuator.

The container is also referred to as a sample application device.

In an option, the base comprises the reagent chamber.

In an option, the base comprises the reagent reservoir.

In an example, the base is a disposable arranged to be used with an analyzer. The base may comprise detecting chamber (s) arranged with interface(s) adapted to the analyzer such that the analyzer can analyze the liquid in the detecting chamber(s) via this interface(s).

In an example, the base is provided as a cartridge and the container is provided as a sample application device, in which the sample can be processed and/or modified to prepare the next processing in the container in view of analysis.

In an example, the base comprises a protruding connection portion for connection with an analysis device.

In an example, the actuator comprises at least one actuator that is movable relative to the housing; and, upon movement, the at least one actuator forces the liquid to flow within the housing towards an analysis device.

In an example, the base is configured for interacting engagement with a lower portion of the container.

According to an example, the actuator comprises a metering actuator configured for supplying at least a part of the liquid from the receiving chamber to the metering chamber to provide the predetermined amount of the liquid. In an option, the metering actuator is provided as a sucking actuator configured for sucking the liquid including the patient's sample from the receiving chamber into the metering chamber. In an additional or alternative option, the metering actuator is also provided as a pressing actuator configured for pressing the liquid out of the metering chamber through the outflow to the reagent chamber.

In an example, an extraction of liquid from the receiving chamber to the metering chamber is performed by suction by creating a negative difference of pressure between the receiving chamber and the metering chamber by the metering actuator; and/or
ii) the supply of the extracted liquid from the metering chamber to the reagent chamber is performed by pressing by creating a positive pressure difference between the metering chamber and an area downstream the outflow.

According to an example, the metering actuator is provided as a cylinder providing the metering chamber, in which a piston is arranged. The cylinder and the piston can be moved in relation to each other to vary a volume of the metering chamber. Further, by varying the volume, the inside of the metering chamber can be loaded with a relative positive or negative pressure.

The metering chamber is defined by the lateral and top sides of the cylinder and by the movable piston.

According to an example, the actuator comprises at least one lever member configured for providing a first manually applied activation force to the metering actuator. The at least one lever member is activatable in a first direction by placing of the housing onto the base such that the at least one lever member is moved relative to the housing due to abutment of the lever member on the base while the base is in interacting engagement with the container. In an option, the at least one lever member is configured to provide a second activation force to the metering actuator when a manual force is applied to the lever member, which second activation force is opposite to the first activation force; wherein the at least one lever member is activatable in a second direction opposite to the first direction by moving of the at least one lever member relative to the housing and the base while the housing and the base are engaged with each other.

In an example, while the base is in interacting engagement with the container, a part of the housing is accommodated in a part of the base.

When the first force is applied to the lever member, the volume of the metering chamber is increasing, and when the second force is applied to the lever member, the volume of the metering chamber is decreasing. The first force results in extracting the liquid into the metering chamber, i.e. sucking the liquid into the metering chamber, and the second force results in extracting the liquid out of the metering chamber, i.e. pressing the liquid out of the metering chamber.

In an example, a device providing a solution for the mentioned problem comprises a receiving chamber for receiving a patient's sample, a first reagent reservoir and/or a second reagent reservoir. The receiving chamber may be configured for receiving a sample or at least an end portion of a sample collecting element, with a patient's sample being collected by means of that sample collecting element. The first reagent reservoir may generally be configured to accommodate a liquid, a jellylike or dry reagent. The reagent may include a lysing agent, i.e. the first reagent may be a kind of a lysis buffer. Likewise, the second reagent reservoir may generally be configured to accommodate a second reagent. The second reagent may be adapted to specifically bind a targeted analyte in the sample or a contaminant in the sample. The reagent may further be bonded to a label allowing or enhancing the analyte detection for diagnosis purpose and/or to an activatable element allowing the driving or transportation of the analyte or the contaminant if the activatable element is activated by means of activation. This activatable element may include magnetic particles, magnetically activated by magnetic means (coils and/or magnets). In an even more particular case, those magnetic particles can also be used as labels. In general, the first reagent may differ from the second reagent.

Further, the device may comprise at least one actuator. The device may comprise a first actuator for putting in contact a first reagent with the sample and a second actuator for putting in contact a second reagent with the sample. The device may comprise an actuator being adapted for supplying a first reagent from the first reagent reservoir to the receiving chamber. The actuator may further or alternatively be adapted for supplying the sample from the receiving chamber to the first reagent reservoir. Furthermore, the actuator may be adapted for supplying the first reagent from the first reagent reservoir and the sample from the receiving chamber to a mixing chamber. The device may comprise an actuator for supplying a second reagent from a second reagent reservoir to the receiving chamber or for supplying the sample from the receiving chamber to the second reagent reservoir. Furthermore, the device may comprise an actuator for supplying the second reagent from the second reagent reservoir and the sample from the receiving chamber to a mixing chamber.

In accordance with an example, an actuator may be provided which is configured for mixing a liquid including the patient's sample with a reagent from a reagent reservoir. The actuator may further be configured for supplying the liquid including both the patient's sample and the reagent to an analysis device.

In accordance with another example, another actuator may be provided which is configured for supplying a reagent from a reagent reservoir to the sample or the sample collecting element so that the patient's sample can be removed from the sample collecting element and so that a mixture is achieved with the reagent and the patient's sample.

It is noted that in cases in which two actuators are provided, the actuators may be indicated as first actuator and second actuator. It is further noted that the terms "first" and "second" are mainly used to denote the actuators. The actuators may also be denoted as "upper" and "lower" actuator or else. Consequently, if a device according to an embodiment as described herein comprises only one actuator, that actuator will not be denoted by a specific term, even if that actuator may be described below as for example "first" or "second" actuator in an embodiment. The same counts for the first and second reagents as well as for the first and second reagent reservoirs, respectively.

In accordance with another example, a device for preparing a patient's sample before analysis may comprise a housing and an actuator, wherein the housing may optionally include a receiving chamber and a reagent reservoir, wherein the receiving chamber is configured for receiving a patient's sample and wherein the reagent reservoir is configured for receiving a reagent. The actuator may be movable relative to the housing and may be configured for extracting a predetermined amount of the liquid received in the receiving chamber and for supplying the extracted liquid to the reagent reservoir, so that the reagent is suspended in the liquid.

In accordance with an example, the device may comprise a metering chamber, wherein an actuator is configured for sucking the liquid including the patient's sample from the receiving chamber into the metering chamber so that a predetermined amount of the liquid may be mixed with a reagent. The mixing of the liquid and the reagent may be improved by a turbulent flow generated by that actuator in the reagent reservoir. This turbulent flow must be enough to generate a better mixing of the reagent with the sample. For example, the actuator may comprise a non-linear flow channel and/or a flow channel with differing cross sections along its length. It will be understood that such a channel may also be provided in a housing of the device. The actuator may be configured to press the liquid into the channel, no matter whether the channel is formed in the actuator and/or in the housing. In other words, the actuator may be configured for transferring a liquid mixture comprising a patient' sample and another reagent from the receiving chamber into the metering chamber, and from the metering chamber to a detection chamber of an analysis device, where the mixture may be analyzed. The device may further include a reagent and/or filter received in the reagent reservoir, for further processing the mixture.

According to an example, the metering chamber of the device may comprise an upper orifice through which the liquid may be extracted from the receiving chamber into the metering chamber, and a lower orifice through which the extracted liquid may be supplied to the reagent chamber. In an option, the first orifice is provided in the cylinder and the second orifice is provided in the piston. In an alternative or additional option, the first orifice is arranged in a lower part of the cylinder such that the first orifice provides a connection between the metering chamber and the receiving chamber once the volume of the metering chamber is increased and an underpressure has been built up. In an alternative or additional option, the second orifice is arranged to be covered with an openable closure that is opened at least partly by an opening member of the base such that the second orifice provides a connection between the metering chamber and the reagent chamber once the liquid has been extracted into the metering chamber and the metering actuator is actuated for pressing the liquid out of the metering chamber.

Preferably, the orifice is defined as a channel or through-hole forming a fluidic path to the outflow in the wall of the actuator, such that a fluid connection can be established between the metering chamber and the receiving chamber.

In an example, the liquid is extracted from the receiving chamber to the metering chamber by extraction, and the extracted liquid is supplied to the reagent chamber by supply.

In an example, the extracted liquid is supplied to a reagent reservoir and/or a detection chamber, i.e. to an analysis device.

In accordance with an example, the actuator for metering the liquid and transferring the liquid in a direction to an analysis device, extends substantially around a longitudinal axis of the device, wherein an actuation of the actuator may be performed in a direction along this longitudinal axis.

According to an example, the device further comprises a pierceable seal being configured to prevent the supplying of the liquid from the metering chamber to the reagent chamber and/or a liquid receiving volume. In an option, a piercing member is provided in the base extending from the base such that upon interacting engagement of the base and the container, and preferably a further movement, the piercing member provides an opening by piercing the seal.

In an example, the seal is provided as a pierceable foil, i.e. pierceable film, e.g. as pierceable membrane. In an example, the membrane is liquid- and air-tight.

The liquid receiving volume may be provided as further chambers or as reservoirs or as supply channels.

In an example, the seal or pierceable membrane is configured to prevent the supplying of the liquid to the reagent reservoir.

In an example, the whole in the seal or membrane is provided smaller than the piston diameter in order to generate the turbulence flow.

In accordance with another example, the outlet of the device may be a channel with the seal or membrane which is pierceable by a piercing element. Alternatively, the outlet channel may be provided in a piercing element designed to pierce a pierceable membrane provided in an analyzing device. In both case, the pierceable membrane is configured to prevent the supplying of the liquid mixture to the analysis device, until the pierceable membrane is pierced.

According to an example, the actuator is further configured to generate a turbulent flow of the liquid, when supplying the liquid to a reagent chamber.

In an example, a closure of the receiving chamber is provided that comprises a cutting portion; wherein the cutting portion is configured for cutting a portion of a sample collecting element which may protrude out of the receiving chamber. The supplying actuator also acts as closing actuator activating the closure of the receiving chamber and as a cutting actuator activating the cutting of the protruding portion of a sample collecting element.

According to an example, the actuator is adapted for putting a reagent in contact with a sample provided in the receiving chamber to provide a liquid including the patient's sample and the reagent. In an option, the actuator is adapted for putting the reagent in contact with the sample to provide a liquid including the patient's sample and the reagent. In a further option, additional or alternatively, the actuator is adapted for supplying the predetermined amount of liquid to an analysis device for analysis purposes.

In an example, the reagent is another reagent.

In an example, the actuator comprises a supplying actuator configured for supplying a reagent from a first reagent supply reservoir to the sample in the receiving chamber; and wherein, preferably, the supplying actuator is configured to decrease a volume of the first reagent supply reservoir, thereby forcing the reagent to leave the first reagent supply reservoir and to enter the receiving chamber; and/or wherein, preferably, the actuator comprises two gripping members configured for providing a manually applied activation force to the supplying actuator.

In an example, the actuator comprises the first reagent supply reservoir provided upstream the metering chamber.

In another example, the actuator comprises a second reagent supply reservoir provided downstream the metering chamber.

As an option, in an example, both the first and the second reagent supply reservoirs are provided.

In an example, the second reagent supply reservoir provided in the base contains magnetic particles that bind RNA or DNA. The first reagent supply reservoir provided in the upper part contains the lysis buffer to be brought into contact with the sample.

In accordance with yet another example, the device comprises an actuator having a metering chamber, wherein the actuator is configured for sucking a liquid from the receiving chamber into the metering chamber and for pressing the liquid out of the metering chamber in a direction to a detection chamber. Between the metering chamber and the detection chamber, a reagent reservoir may be provided, being configured for receiving a reagent, wherein the reagent can be suspended in the liquid, when the liquid is pressed from the metering chamber through the reagent reservoir and to the detection chamber. The reagent may be a dried or solid reagent, preferably a magnetic reagent.

In accordance with a more particular example, a filtering component may be arranged between the metering chamber and the detection chamber, so as to filter some elements of the liquid. The filter component may be provided in a liquid path, between the receiving chamber and the analysis device, wherein the actuator may be arranged such that a transfer of the liquid from the receiving chamber goes through the filter when the actuator is actuated.

As a further option, this filtering component can be designed such that it provides a mechanical resistance to the actuator.

The device may be a disposable device.

A device in accordance with another example may comprise a housing and an actuator. The housing may include a receiving chamber and a reagent reservoir, wherein the receiving chamber is configured for receiving a sample or at least a portion of a sample collecting element with a sample and wherein the reagent reservoir is configured for receiving a reagent. The actuator may be movable relative to the housing and may be configured for sequentially closing the receiving chamber and putting in contact the reagent received in the reagent reservoir with the sample of the receiving chamber. The actuator may alternatively or further be configured for supplying the reagent from the reagent reservoir to the receiving chamber or for supplying the sample from the receiving chamber to the reagent reservoir. The actuator may also be configured for supplying the reagent from the reagent reservoir and the sample from the receiving chamber to a mixing chamber. The device is advantageously further configured to mix the patient's sample with the reagent. This operation may be particularly performed such that, when a sample collecting element (e.g. a swab) with a patient's sample is in the receiving chamber, the patient's sample is at least partially removed from the sample collecting element.

The reagent may be inserted into the reagent reservoir by a means which is capable of holding the reagent. If the reagent is a liquid or jellylike reagent, the means for holding the reagent may be a sponge, an elastic pad or bag, or a vial. Depending on the kind of the means for holding the reagent, the actuator for supplying the reagent to the sample collecting element, may be configured to squeeze the sponge, or to press the bag or pad, which may be a closed bag or pad, until it bursts to release the reagent, or to break the hard vial to release the reagent. If the reagent is dry, the reagent may also be hold in a bag, pad or vial.

In other words, the second function of the actuator of the device can be seen as to put into contact a reagent, for example a dry or liquid lysis reagent, with a liquid or dry patient's sample so as to allow the reagent to chemically and/or mechanically react with the sample. It will thus be understood that a liquid patient's sample may come into contact with a dried reagent and a more or less dry patient's sample may come into contact with a liquid reagent.

In accordance with an example, the actuator may further be configured for sealing the receiving chamber and/or for encapsulating the sample collecting element. The actuator may comprise a closing element, wherein the closing element includes, for example, a surface which will cover an opening of the receiving chamber upon movement of the actuator relative to the housing, through which opening a patient's sample and/or at least a portion of a sample collecting means like a swab may be inserted into the receiving chamber of the housing. The closing element may be a separate element which is fixedly attached to the actuator or may be integrally formed with an actuator body.

In accordance with an example, the actuator may comprise a closing element and an actuation means, the closing element may be arranged to close the receiving chamber and the actuation means may be arranged to supply the reagent to the patient's sample. The closing element may comprise two elements which move one to the other, when the actuator is actuated, so as to close the opening, the two closing elements are each provided by gripping members. The actuation means may surround the closing element and may be designed to rotate about the central axis of the housing so as to supply the reagent and to perform the removal of the sample from the sample collecting element. The actuation means may be an internal wall onto which the sample collecting element may be pressed when the actuator is rotated so as to remove said sample from the sample collecting element.

In accordance with an example, the actuator may further be configured for cutting a portion of a sample collecting element which may protrude out of the receiving chamber. The actuator may comprise a cutting element which may be attached to an actuator body or which may be formed integrally with the actuator body, i.e. which is part of the actuator body.

In accordance with an example, a sharp edge for cutting the sample collecting element may be provided at a closing element for closing the receiving chamber, so that firstly a portion of the sample collecting element which portion protrudes out of the housing, can be cut, and that secondly a further movement of the actuator will close the receiving chamber in the housing. A sealing element may be provided to not only close but seal the housing. After cutting a portion of the sample collecting element and closing and/or sealing the receiving chamber, the actuator may supply the reagent from the first reagent reservoir to the sample collecting element.

In accordance with a further example, the actuator may be further configured to move along a circumference of the receiving chamber.

It will be understood that the receiving chamber may be big enough to completely accommodate a patient's sample or a sample collecting element like a swab without stem. But in case a sample collecting element is intended to be used which element comprises a long stem, such a stem may be cut by, for example, a sharp edge at the actuator.

It will further be understood that the device will have upper and lower portions, as a liquid is used inside the device, which liquid may flow and may be transferred in an appropriate way, only when the device is in an adequate orientation. A main axis of the device may be a vertical axis and a movement about the circumference may be considered as a rotational movement about the vertical axis of the device.

The device in accordance with an embodiment may further comprise a blocking element being configured for blocking a reverse movement of the actuator after the receiving chamber is closed by the actuator. For example, a blocking element may include an elastic element of a snap-on connection or may have a plurality of teeth or hooks like a ratchet mechanism, allowing a movement only in one direction.

In accordance with an example, a further provided actuator may be configured to block any movement of the mentioned actuator, until the further actuator reaches its final position, i.e. has caused a reagent to be supplied to the sample in the receiving chamber. For example, the element which may squeeze a lysis buffer pouch in a first reagent reservoir may block the movement of the metering chamber for drawing the liquid out of the receiving chamber.

In accordance with an example, the device is configured to be used only once. In particular, the actuator may only be actuated once, i.e. moved relative to the housing. The first actuator may be in a blocking position in which a reverse movement of the first actuator is not possible, wherein the blocking position may be reached as soon as the receiving chamber is tightly closed by the actuator.

According to the invention, also a system for analyzing a patient's sample is provided. The system comprises a sample preparation device provided as a device according to one of the preceding examples, and a sample analysis device configured to conduct at least one analysis of the liquid provided by the preparation device.

According to the invention, also a method for preparing a patient's sample before analysis is provided. The method comprises the following steps:

a) receiving a sample in a receiving chamber;
b) putting a reagent in contact with the sample thus providing a liquid including the patient's sample and the reagent; and
c) supplying the liquid to an analysis device for analysis purposes.

In accordance with another example, a method of using a device as described above may comprise the steps of providing a first reagent and inserting the first reagent into the first reagent reservoir, receiving a sample or at least a portion of a sample collecting element with a sample in the receiving chamber, closing the housing of the device, supplying the first reagent to the patient's sample so as to generate a liquid mixture including the patient's sample and the first reagent. The method may further comprise the step of sealing the receiving chamber, and be yet further comprise the step of cutting a portion of the sample collecting element which protrudes out of the receiving chamber, in case a sample collecting element is used.

In accordance with an example, a method of using a device as described above may comprise the steps of receiving a liquid in the receiving chamber of the housing, extracting a predetermined amount of the liquid from the receiving chamber, supplying the metered liquid to a reagent reservoir, and mixing the liquid with a reagent received in the reagent reservoir. All these steps may be implemented by actuating an actuator in a single operation. The step of supplying the metered liquid to the reagent reservoir may include generating a turbulent flow of the liquid. The method may further comprise the steps of receiving a patient's sample in the receiving chamber, wherein the step of receiving the liquid in the receiving chamber includes the step of applying a reagent to the patient's sample to generate a mixture of the patient's sample and the reagent.

The aspects defined above and further aspects, features and advantages of the present invention may also be derived from the examples of embodiments to be described hereinafter and are explained with reference to examples of embodiments.

BRIEF DESCRIPTION OF THE DRAWINGS

The invention will be described in more detail hereinafter with reference to examples of embodiments but to which the invention is not limited:

FIGS. 17 to 19 illustrate the steps for supplying the liquid from the metering chamber to a receiving volume, wherein FIG. 17 shows a piercing of a seal.

The illustration in the drawings is schematically only and not to scale. It is noted that similar elements are provided with the same reference signs in different figures, if appropriate.

DETAILED DESCRIPTION OF EMBODIMENTS

Figure 1:
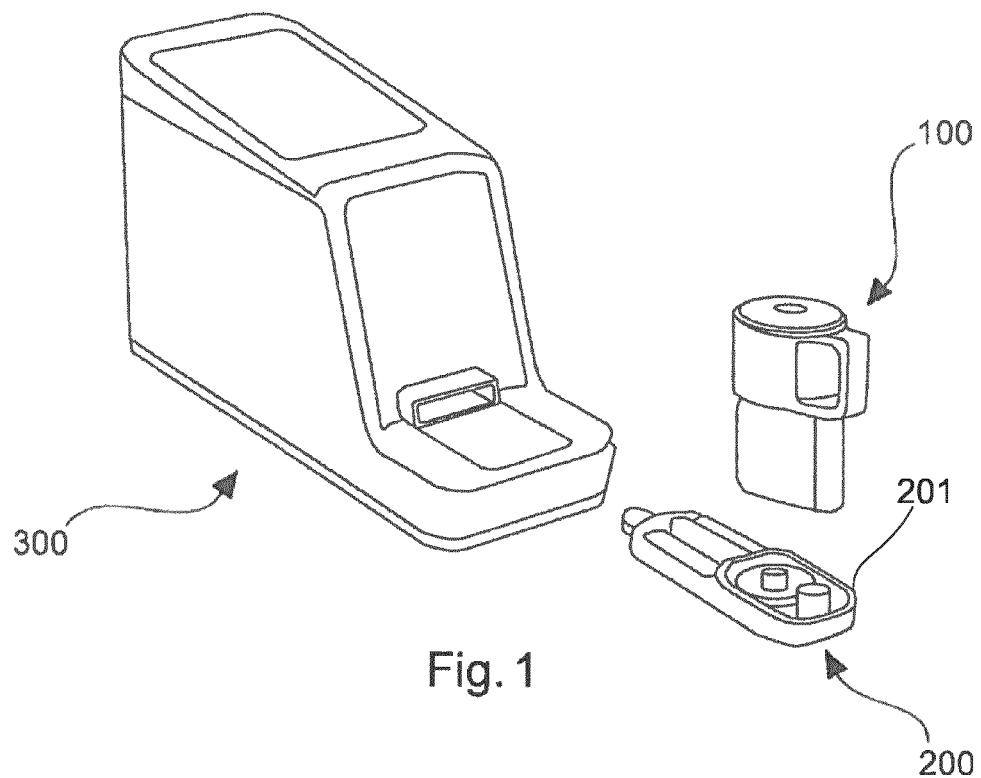
FIG. 1 illustrates a schematic setup of a system for molecular analysis.

A solution for receiving and processing for example a swab with a patient sample fulfills three requirements: high ease-of-use, low cost and safe sample containment. Low costs can be achieved by a device which is as small as possible. Since only the tip of a swab contains patient material, the tip may be separated from the stem. Removing the stem of the swab additionally helps to achieve a ratio of internal chamber volume and liquid that is favorable for efficient rinsing of the swab by minimizing dead volume. The cutting of the swab stem can be carried out by using a separate blade like a knife or by making use of an integrated cutting mechanism. Existing solutions often require an additional liquid transfer step during which the acquired eluate is removed from the container that contains the swab, thereby increasing the risk for contamination. To decrease this risk, it is suggested to fully contain the tip of the swab within the device after removing the stem and rinsing it.

Consequently, essential sample preparation steps, including the cutting of the stem of the swab, may be transferred into a disposable sample application device that may be manually operated by the user. The creation of a sample application device in combination with a main cartridge separates macrofluidic and microfluidic operations and thereby makes it possible to optimize the designs of the sample application device and the cartridge almost independently while offering high ease-of-use.

It is further suggested that a device enables an inexperienced or untrained user to process a patient sample that has been obtained for example with a nasal swab. The user may first insert a swab through an opening into the device. By twisting handles of the device, the user may firstly shorten the swab, may then release a small amount, approximately a milliliter volume of lysis buffer and rinses the swab in the released buffer. The device may then be connected with a cartridge which may previously been inserted into an analysis device. By only two additional actuation steps, the user may pump the rinsing buffer into a metering chamber before ejecting it from the device into the cartridge. In this last step, the liquid may be passed through a gDNA filter and forced into turbulent contact with dried magnetic particles that, once suspended, capture RNA molecules from the sample volume. These particles may then be collected by a magnet to undergo further processing.

The binding of nucleic acids to silica particles is limited by the capacity of the particles, i.e. the available surface area. During a binding step, background and target nucleic acids are in competition. To ensure that the yield of the extraction step is not limited by the amount of available surface area, it is possible to either increase the available surface area by adding more particles to the reaction or to reduce the amount of background material.

For extraction processes, the total amount of magnetic silica particles may be limited by the dimensions of the fluidic system. Larger particles may be more difficult to control due to their tendency to split when actuated by a magnetic field. In addition, the elution of targets from the particles has been shown to become less efficient as the particles occupy a larger part of the elution volume.

Alternatively, it is possible to keep the amount of particles constant and to reduce the concentration of background species. In assays that extract material from cells to analyze RNA, genomic DNA is a major background component that significantly reduces the available capacity for RNA binding. To free up additional binding capacity, it is therefore desirable to selectively remove genomic DNA from the sample before mixing it with magnetic silica particles to initiate the binding phase.

Removal of gDNA can be achieved by using treated silica filters that selectively bind DNA under suitable buffer conditions (low pH, high ionic strength) while allowing RNA to pass. These filters are commonly used to extract DNA for future analysis (e.g. Qiagen kit). In these applications, the DNA is first bound and afterwards eluted from the filter. For example, a filter may be used to remove DNA in order to improve subsequent RNA sample preparation and detection steps.

A disposable device is proposed that can be manually operated to carry out steps of the sample preparation procedure in a simplified manner. The device may comprise a chamber which receives a patient sample (crude lysate) in which nucleic acids are available in solution. To efficiently capture the nucleic acids from this volume, the magnetic particles are preferably dispersed homogeneously and rapidly throughout the sample.

At least some of the following requirements are fulfilled by the proposed device. The particles may be stored in the device in freeze-dried spheres that dissolve rapidly upon contact with the liquid. For improved downstream processing, the sample can be passed through at least one filter structure before getting into contact with magnetic particles. The fluidic resistance of the combined filter structures may be overcome by the pressure difference that drives the fluid transport. All steps may be executed with only few user interactions and without risk of sample contamination or potentially harmful exposure to the user. The time allowed for capturing target molecules with the particles may be controlled. The mixing process may not be carried out by manual agitation of the disposable to avoid human error. The device may be connectable to a cartridge in which further downstream processing occurs.

This device according to the described embodiments addresses at least some of this set of requirements by integrating several fluidic steps in a single device that contains the fluidic system and manually triggering their execution. The device may be used in combination with a main cartridge that may contain a microfluidic system for further downstream processing of the sample.

In a first handling step, a fluidic connection between the device and the main cartridge may be established and a metered amount of patient sample liquid may be drawn into a chamber via a small opening. In a second step, the chamber may be compressed and a liquid may thus be ejected through an opening. The generated pressure may be sufficient to force the liquid through optional filter structures and through a narrow section of the fluidic path. In the narrow section, the liquid is accelerated and ejected into a small cavity that holds a portion of dried particles and may have a total volume that is much smaller than the total volume of the sample. The high velocity of the liquid effectively agitates the particles and thereby aids their rehydration and dispersion. Upon passing through the chamber with the particles, the liquid may be pushed through a further narrow section before being again ejected into a collection chamber that may also be the first chamber of the main cartridge. During ejection, the fluid undergoes (chaotic) mixing whereby the particles are homogeneously distributed throughout the total volume of the sample. The arrival of the sample mixture in the main cartridge can be detected by the instrument and marks the start of the binding process. After the binding process is finished, the instrument may automatically carry out subsequent steps of sample preparation and detection.

A device in accordance with an embodiment may comprise a first multi-step mechanism that is suitable for receiving a patient's sample to firstly cutting an elongated stem (if necessary), secondly sealing the sample in a chamber, thirdly opening a reservoir with a liquid or dry reagent, inside the device and fourthly releasing the reagent from the reservoir into the chamber. The device may further comprise a second mechanism for ejecting a liquid including the reagent as well as the patient's sample from the device into a fluidic cartridge.

In accordance with an embodiment may the device be used by manually operating a first and/or a second mechanism such that the intended positions of the mechanisms are reached in a pre-defined and irreversible order and that the inserted swab and the released liquid are safely contained within the device.

It will be understood that the stem may be a part of a nasal or nasopharyngeal swab and the inserted end of the swab comprises an area which is suitable for obtaining a patient sample. Furthermore, the internal reagent reservoir may be a flexible pouch.

FIG. 1 is an illustration of an embodiment of a system for molecular analysis allowing molecular diagnostics for a physician based on a tissue sample. The system includes a container 100, a cartridge 200 (or base 200) as well as an analysis device 300. The container 100 is adapted to be connected with an end portion of the cartridge 200 so as to allow a fluid to be transferred from the container 100 to the cartridge 200. The cartridge 200 is adapted to be at least partially inserted into the analysis device 300. In the analysis device 300, the sample which may be in a liquid, may be processed so as to achieve data characterizing the sample and allowing a physician to provide a diagnosis.

The system of FIG. 1 can also be referred to as a system for analyzing a patient's sample. Such system comprises a sample preparation device provided as a device according to one of the examples described below, e.g. as the mentioned container 100 with the base provided as the also mentioned cartridge 200. Further, a sample analysis device configured to conduct at least one analysis of the liquid provided by the preparation device is provided, such as the analysis device 300.

Figure 2:
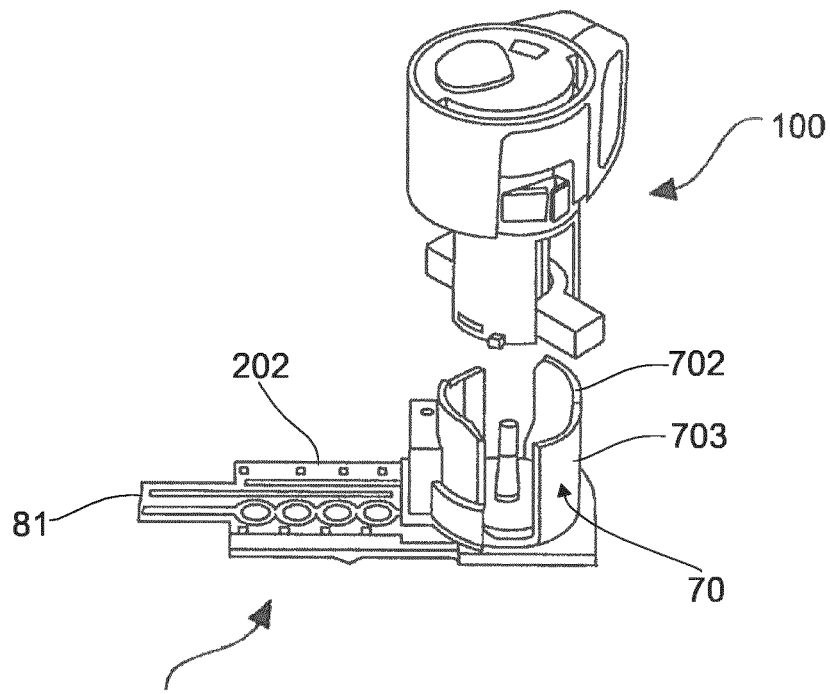
FIG. 2 shows parts of a system for molecular analysis.

FIG. 2 shows an embodiment of parts of a system for molecular analysis in more detail. The container 100 comprises a kind of a grip portion and an upper part of the container as well as an element which looks like a stem protruding through a lower part of the container. The cartridge 200 comprises a kind of a hollow cylinder which is slotted so as to allow the lower part of the container 100 to be accommodated in that cylinder with the stem like element protruding out through the slot in the cylinder of the cartridge. The other end of the cartridge 200 is formed like a tongue which has a reduced width protruding from the end of the cartridge 200. Such a tongue may be configured to be in contact with a structure inside an analysis device.

FIG. 1 shows a first example 201 of the cartridge 200. In FIG. 2, a second example 202 of the cartridge 200 is shown.

Figure 3:
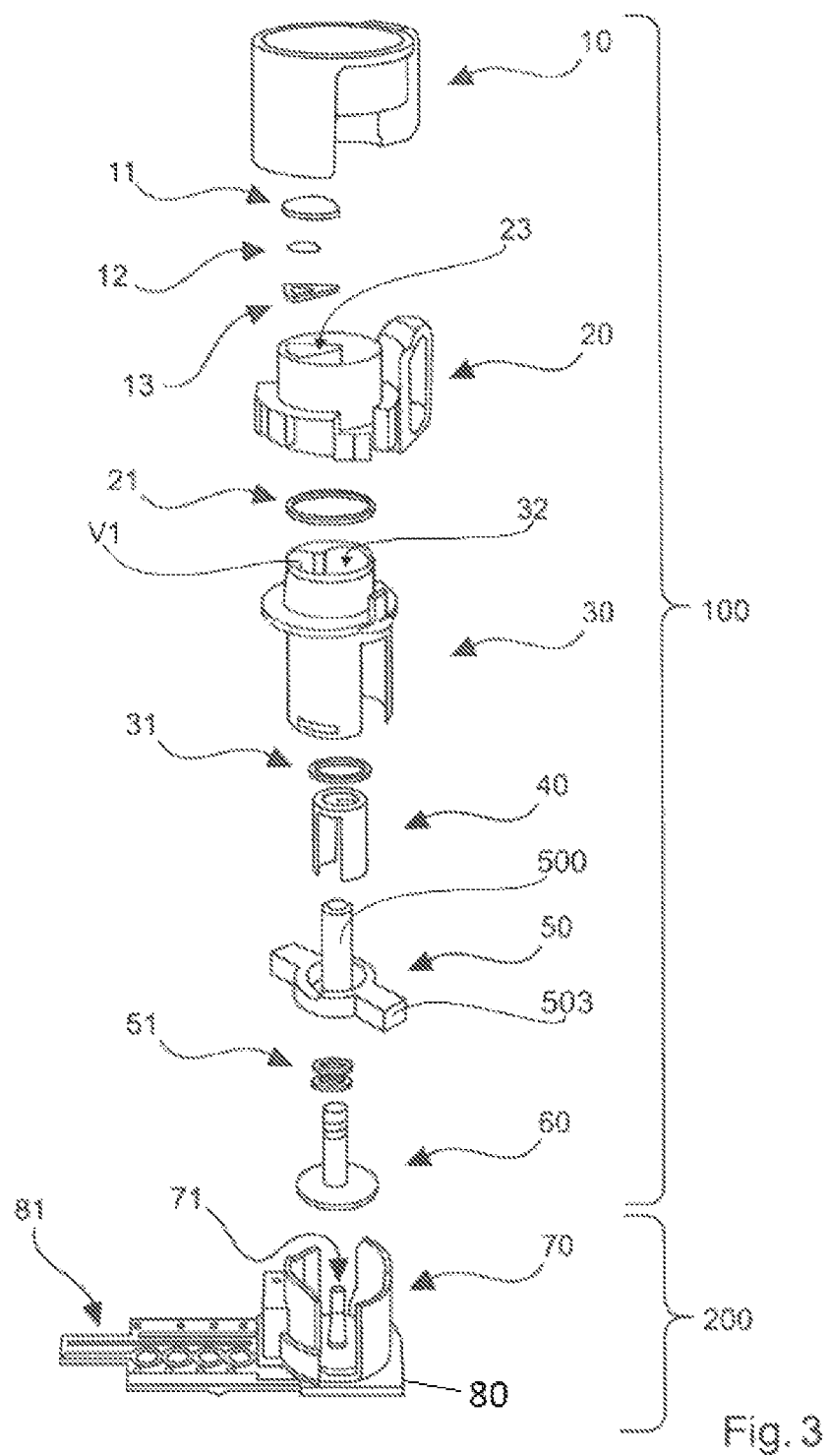
FIG. 3 is an exploded assembly drawing of parts of a system for molecular analysis as shown in FIG. 2.

FIG. 3 is an exploded assembly drawing of parts of a system for molecular analysis. The system comprises the sample preparation device and the sample analysis device. The sample analysis device 300 is configured to conduct at least one analysis of the liquid provided by the preparation device. However, the sample analysis device is not further described in detail. FIG. 3 describes the sample preparation device, comprising the container 100 with housing 10, 30; and an actuator described in more detail below. The housing includes a receiving chamber 32 and a reagent reservoir (not shown in FIG. 3). The receiving chamber is configured for receiving a sample and the reagent reservoir is configured for receiving a reagent. The actuator is adapted for putting the reagent in contact with the sample to provide a liquid including the patient's sample and the reagent. The actuator is further adapted for supplying the liquid to an analysis device for analysis purposes.

In an example, the container 100 and the base, i.e. the cartridge 200, are provided as separate parts that are configured to be temporarily assembled together during a sample preparation process. The base comprises an interface configured for mating engagement with a lower portion of the housing. The base comprises at least one liquid receiving volume (indicated with little circles) into which the liquid is supplied by the actuator. The base may further comprise a protruding connection portion for connection with an analysis device. The base is provided as a cartridge and the container is provided as a sample application device.

The actuator comprises a supplying actuator, also referred to as first actuator 20, configured for supplying the reagent from the reagent reservoir to the sample in the receiving chamber. The supplying actuator is configured to decrease a volume of the reagent reservoir, thereby forcing the reagent to leave the reagent reservoir and to enter the receiving chamber. The actuator comprises two gripping members configured for providing a manually applied activation force to the supplying actuator.

In an example, the first actuator 20 is aimed at lysing the sample with a lysing reagent. This lysing reagent may be different that a reagent added downstream the metering chamber. This reagent downstream may also be referred to as a "specific reagent") which is a reagent adapted to bind certain analytes in the lysed liquid sample.

The reagent in may be a lysing agent.

During the sample preparation in the sample application device, magnetic silica particles may be provided to bind specifically to RNA or DNA.

The actuator comprises at least one actuator that is movable relative to the housing. Upon movement, the at least one actuator forces the liquid to flow within the housing towards the analysis device.

The actuator further comprises a metering chamber 52 (see below) configured for receiving a predetermined amount of the liquid.

The metering chamber 52 has a volume that can be changed by the action of the actuator (as described in exemplary embodiments below).

The actuator also comprises a metering actuator, also referred to as second actuator 50, configured for supplying supply at least a part of the liquid including the patient's sample and the reagent from the receiving chamber to the metering chamber to provide the predetermined amount of the liquid. The metering actuator is provided as a sucking actuator configured for sucking the liquid including the patient's sample from the receiving chamber into the metering chamber. The metering actuator is also provided as a pressing actuator configured for pressing the liquid out of the metering chamber in a direction to a detection chamber.

Preferably the actuator 50 is provided with at least one handle 503 such that the actuator 50 is movable relative to a piston portion formed at a top end portion of the connection element 60. As for example illustrated in FIG. 3 the actuator comprises two handles at opposite positions on the circumferential wall 500 defining the metering chamber 52.

The piston is provided by arranging the second actuator 50 and the connection element 60 one to the other such that the metering chamber 52 is defined between the two having a volume adjustable by the relative movement of the second actuator 50 and the connecting element 60 (see also FIGS. 11 and 12A to 12D).

What is meant is that the total stroke of the piston defines the maximum volume of liquid that is extracted from the first chamber. Preferably, the piston is fully displaced, to avoid that less volume would be extracted, as in this way the volume is better controlled as it is determined by the geometry of the device, and not by the way it is used.

In an embodiment not shown the suction opening 53 of the actuator 50 is additionally provided with a filter element for filtering impurities provided with the sample collecting element. Additionally, a valve can be incorporated into the suction opening which opens when a predetermined suction force is established within the metering chamber.

In particular, the elements of the container 100 according to an embodiment are shown in FIG. 2. Mainly, the container 100 comprises a first housing part 10, a second housing part 30, the first actuator 20, the second actuator 50, and a connecting element 60.

The first housing part 10 is formed as a capping piece having a substantially cylindrical shape and being hollow. Furthermore, the first housing part 10 comprises a portion with an open sidewall. The first housing part 10 also comprises a first handle (see for example reference sign 16 in FIG. 6).

The first actuator 20 also includes a substantially cylindrical portion, wherein an outer diameter of that cylindrical portion is smaller than a diameter of the first housing part 10. Furthermore, the first actuator 20 comprises a second handle, which handle protrudes outwardly from that cylindrical portion with a gap between that cylindrical portion and the handle. The first actuator 20 is configured to be assembled with the first housing part 10 so that the cylindrical portion of the first actuator 20 fits into the inner space formed by the cylindrical portion of the first housing part 10. When the first actuator 20 is assembled with the first housing part 10, the wall of the first housing part 10 engages the gap between the cylindrical portion and the handle of the first actuator 20, which handle of the actuator can be denoted as second handle. The cylindrical portion of the first actuator forms a space for also accommodating a portion of the second housing part 30.

The second housing part 30 comprises an upper portion and a lower portion. The upper portion is substantially cylindrical with an outer diameter which is slightly smaller than an inner diameter of the cylindrical portion of the first actuator 20, so that the upper portion of the second housing part 30 fits into the first actuator 20. The second housing part 30 forms a shoulder or flange between the upper portion and the lower portion, with this shoulder or flange closing the space between the first and second housing parts and/or the actuator 20, i.e. closing the inner space of the housing including the receiving chamber 32.

In an assembled condition, the first housing part 10, the first actuator 20 and the second housing part 30 may be rotatable relative to each other about a longitudinal axis of the housing parts. For example, the first actuator 20 may be rotated relative to the first and second housing parts 10, 30 so as to cut a swab stem and close/seal the receiving chamber, with the housing parts 10, 30 stationary relative to each other. Subsequently, the first actuator may be rotated further relative to the housing parts so as to release a first reagent. Alternatively, the first housing part 10 may be moved together with the first actuator 20 relative to the second housing part 30 so as to release the first reagent into the receiving chamber.

It must be noted that the cutting of the swab is shown as an option.

The lower portion of the second housing part 30 is adapted to accommodate the second actuator 50, i.e. the metering actuator, as well as an intermediate guiding element 40 and a connecting element 60. The second actuator 50 comprises in particular a hollow cylinder (referred to as 52 in FIG. 6) and grip portions protruding sidewardly from the cylinder. The connecting element 60 comprises a pin like element protruding from a base plate, wherein the pin like element is adapted to fit into the hollow cylinder of the second actuator 50. In an assembled condition, the second actuator 50 may be moved in an axial direction of its cylinder orientation over the length of the pin like element of the connecting element 60 and guided by the guiding element 40 within the lower portion of the second housing part 30.

The pin like element is formed as a piston within the cylinder. The cylinder and the piston are movably in relation to each other.

As indicated in FIG. 3, spaces or gaps formed by different parts of the container 100 are sealed by sealing elements, such as O-ring sealings. For example, a first seal 21 is provided between the second housing part 30 and the first actuator 20. A second seal 31 is provided between the second housing part 30 and the guiding element 40. Further, at least one further seal 51 is provided between the pin like element of the connecting element 60 and the second actuator 50, i.e. between the piston and the cylinder. For example, two O-ring sealings.

The seal 51 can be an O-ring. In the embodiment shown in FIGS. 3 and 11 the connection element 60 includes at least one circumferential groove 64 for receiving and supporting the O-rings 51. In the shown embodiment two O-rings and two recesses 64 are provided to ensure a better sealing and to ensure that the metered liquid has entered the metering chamber via a filter 63 provided in a receiving opening 68 of the connection element 60. In another embodiment, the seal can be provided by at least one sealing lip surrounding the circumferential wall of the metering chamber.

Further shown in FIG. 3 is an embodiment of the cartridge 200 with an interface element 70 and a bottom plate 80. The interface element 70 is adapted to engage with the lower portion of the second housing part 30, with a cylinder like structure 703 having sideward slots 701 (see FIG. 20) which correspond to the slots in the lower portion of the second housing part 30, so that the gripping portions of the second actuator may protrude through the slots in the interface element 70. The interface element 70 further includes a piercing element 71 which is adapted to engage with the connecting element 60 and is adapted to pierce a seal, e.g. a pierceable membrane provided in the connecting element 60 (i.e. the piston), allowing a fluid flow out of the container 100 and into the cartridge 200. The bottom plate 80 includes a tongue 81 which allows an appropriate connection of the cartridge 200 with an analysis device.

Figure 4:
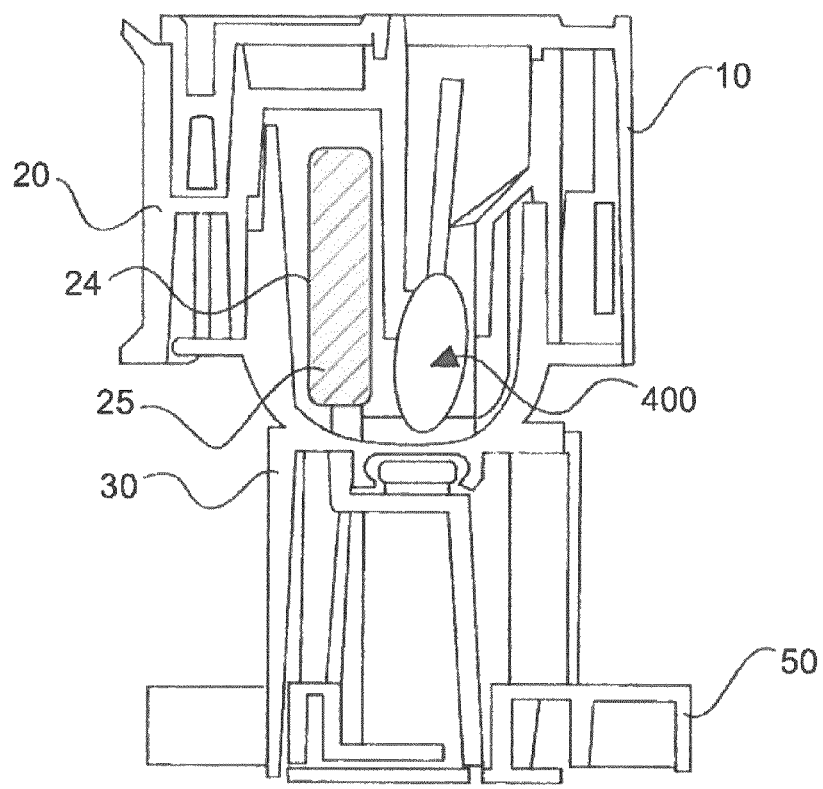
FIG. 4 is a sectional view of a part of a system for molecular analysis, in a first condition corresponding with a sequence shown in FIG. 5 in state B.

FIG. 4 is a section view of an assembled container according to an embodiment. The container comprises the first housing part 10, the first actuator 20, the second housing part 30 as well as the second actuator 50. Having in mind that the container is substantially cylindrical, a swab 400 is placed more or less in a central portion forming a receiving chamber. Beside that swab, a first reagent reservoir 24 is visualized, which first reagent reservoir may be a closed elastic bag filled with for example a liquid reagent 25. It is noted that FIG. 4 shows a container in a condition almost at the very beginning of a method of use of the container. In fact, merely the stem of the swab may have been cut and possibly the receiving chamber may have been closed at that stage.

Figure 5:
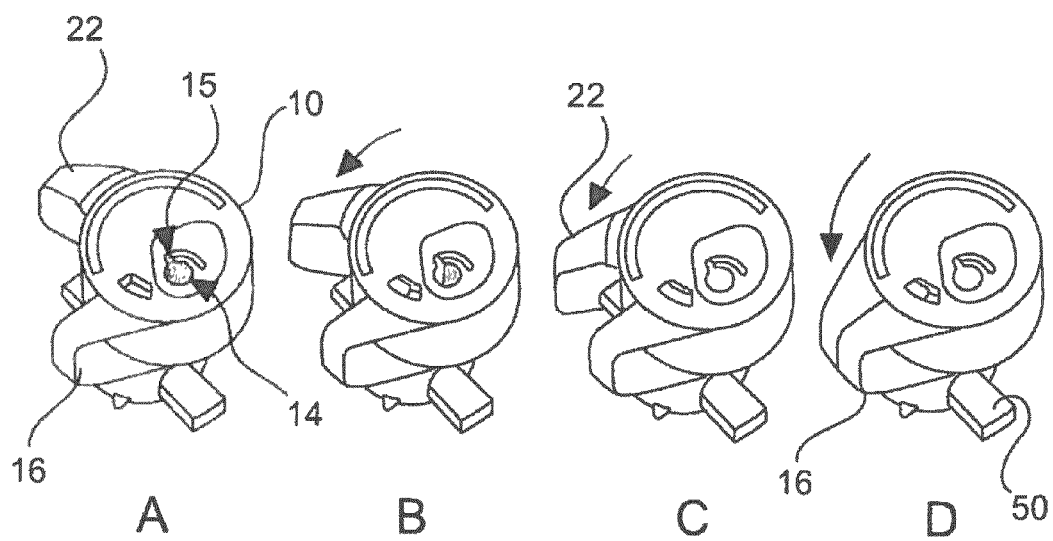
FIG. 5 illustrates a sequence of moving elements of a supplying actuator of a part of the system for molecular analysis shown in FIGS. 2 and 3.

FIG. 5 shows a sequence A, B, C, D illustrating an actuation of the first actuator 20. As can be seen from a comparison of the illustrations in the sequence, the handle 22 of the actuator 20 moves along the circumference of the housing part 10. For ease of use the housing part 10 also comprises a handle 16. At the beginning, in the positions of illustration A, the handle 22 is approximately a quarter of the circumference away from the handle 16. In this stage, a receiving opening 14 and a cutting opening 15 on the top of the first housing part 10 is open, allowing the introduction of a patient's sample for example by means of a swab as sample collecting element. As soon as the swab is placed in the container, i.e. in the receiving chamber of the container, the actuator is moved along the circumference of the first housing part 10 as indicated by the arrows in FIG. 5, firstly closing the cutting opening 15 (illustration B) and subsequently closing the receiving opening 14 (illustration C). In the final position in illustration D, both handles are arranged close to each other with the result that the receiving chamber is completely closed. In the state of illustration D of FIG. 5, the first reagent may already be released from the first reagent reservoir, as shown in FIG. 6.

Figure 6:
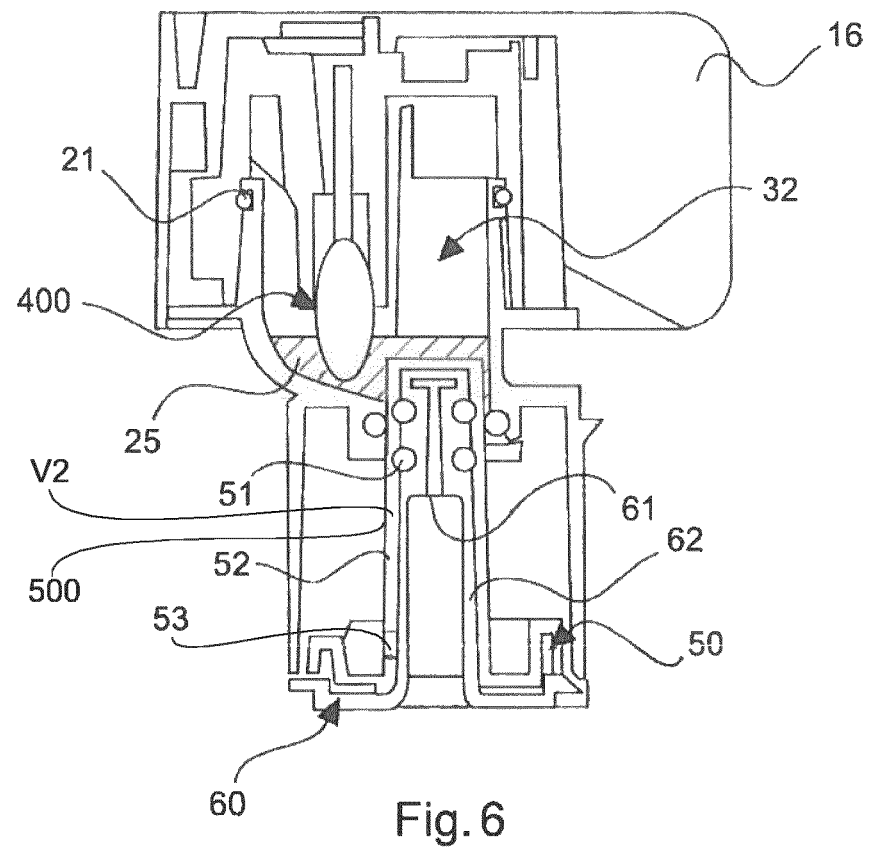
FIG. 6 is a sectional view of a part of the system for molecular analysis, and a second condition corresponding with a sequence shown in FIG. 5 in state D.

FIG. 6 is a sectional view of a container according to an embodiment in a state different from that of FIG. 4 and also viewed from another side as in FIG. 4. In FIG. 6, the first actuator has already been rotated about the vertical axis of the container. Thus, the first reagent 25 is no longer in the first reagent reservoir but substantially at the bottom of the receiving chamber 32. An embodiment of a supplying element 23 for releasing the first reagent is shown in FIG. 3. The supply element 23 comprises a wall portion integrally formed by the actuator 20, wherein the supplying element 23 is suitable for extracting the first reagent from the first reagent reservoir by squeezing the first reagent reservoir upon movement of the actuator. The swab 400 may be rinsed with a liquid reagent so that the patient's sample is solved in the liquid for further processing. Otherwise, a liquid patient's sample may be mixed with a dry first reagent. In both cases, a liquid will be in the receiving chamber including a patient's sample as well as the first reagent, wherein the resulting liquid can be sucked into the metering chamber of the second actuator.

As a further functionality, the supplying element 23 may block an upward movement of the second actuator 50, until the first reagent is extracted from the first reagent reservoir. The supplying element 23 may extend through the body of the first actuator 20 in a longitudinal direction of the actuator (and the housing) so that a bottom wall or surface of the supplying element can be arranged at a level in close vicinity to the top surface of the metering chamber 52 of the second actuator 50, when the device is in an assembled condition. The supplying element 23 will pivot closely above the top surface of the metering chamber 52 upon movement of the first actuator relative to the housing, so that the bottom wall of the supplying element blocks an upward movement of the second actuator. Further, the bottom wall may be dimensioned such that the bottom wall will pivot sidewardly away from the top surface of the metering chamber as soon as the movement of the first actuator is at least almost completed, i.e. as soon as at least 80% of the movement of the first actuator is completed.

Further illustrated in FIG. 6 are seals 21 and 51. A seal 21 is arranged between the second housing part 30 and the first actuator 20 to seal the receiving chamber. Seals 51 are arranged between the connecting element 60 (the piston) and the second actuator 50 (the cylinder).

Hence, the piston is arranged as maintaining its position, whereas the cylinder is arranged as moving part. The relative movement of the piston in relation to the cylinder is thus provided by moving the cylinder.

In particular, seals 51 are arranged in respective grooves 64 at an upper portion of the pin like element 62 of the connecting element 60, so that these seals are fixed in place. On the other side, the cylindrical portion of the second actuator 50 forming the metering chamber 52 is movable along the pin 62 and upwardly into the receiving chamber 32. Thus, when the actuator 50 is moved upwardly, the metering chamber will provide an increasing space above the seals 51 forming at least a reduced pressure, preferably a vacuum in the metering chamber 52. Such a vacuum will cause the liquid in the receiving chamber to be sucked through a side opening 53 (also referred to as first orifice) and into the metering chamber. In an example, the opening is provided at a lower section of the metering chamber 52.

In an example, the connection between the metering chamber and the receiving chamber is provided once the volume V2 of the metering chamber is increased and an underpressure has been built up.

Also, a second orifice 68 is provided through which the extracted liquid is supplied to the liquid receiving volume (indicated with little circles) in the base/cartridge 200. The second orifice is arranged in the connecting element 60, i.e. the piston, and is covered with an openable closure that is opened at least partly by an opening member of the base such that the second orifice communicates with the liquid receiving volume of the base once the liquid has been extracted into the metering chamber and the metering actuator is actuated downwardly for pressing the liquid out of the metering chamber through the second orifice. As indicated above, the closure is provided as the pierceable membrane and the opening is provided by a piercing member.

The opening in the membrane, is preferably generated by the piercing element. In another embodiment, the opening can be permanent; when the opining is permanent, preferably, there is provided a valve.

In both cases the opening is located between the outlet/outflow of the metering chamber and the inlet/inflow of the base.

The base is provided with fluidic path extending from a base opening to the liquid receiving volume. The base opening to be tightly positioned with the second orifice 66 of the connecting element 60. Preferably, a pierceable membrane is provided on the second orifice, and the base is provided with a hollow piercing member in communication with said fluidic path, such that said liquid is transferred from the metering chamber 52 to the base once the pierceable membrane is pierced. Preferably, the piercing element 71 is provided on top of a mating member arranged in the base to mate the connecting element to the base.

Figure 7:
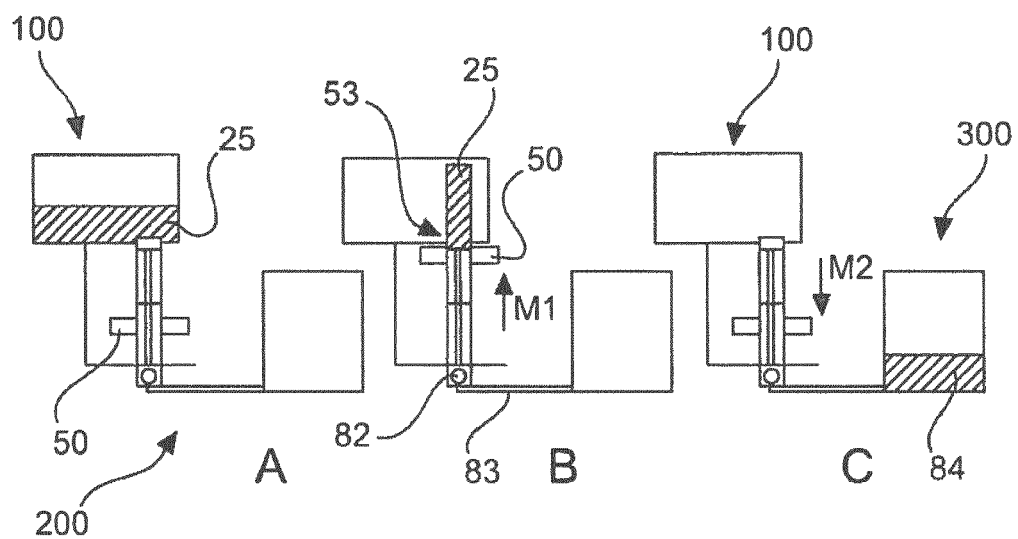
FIG. 7 illustrates a sequence of moving elements regarding a metering actuator of parts of a system for molecular analysis shown in FIGS. 2 and 3.

FIG. 7 shows a sequence A, B, C illustrating an actuation of the second actuator 50. The state of the second actuator relative to the receiving chamber with the liquid 25 is comparable with the state illustrated in FIG. 6. The second actuator 50 is in the starting position. Then, the actuator 50 is moved upwardly, i.e. in a direction of arrow M1 in illustration B of FIG. 7, until the side opening 53 reaches the receiving chamber so that the fluid 25 is sucked out of the receiving chamber and into the metering chamber of the actuator 50. Subsequently, the actuator can then be moved downwardly, as indicated by arrow M2 in illustration C of FIG. 7. By that downward movement, the liquid is pressed through the pin 62 and in a direction to a liquid receiving volume downstream, for example a reagent reservoir 82, and from that liquid receiving volume or reagent reservoir through a channel 83 to a detection chamber 84 for analysis of the liquid. The detection chamber 84 may be located in an analysis device 300.

Figure 8A:
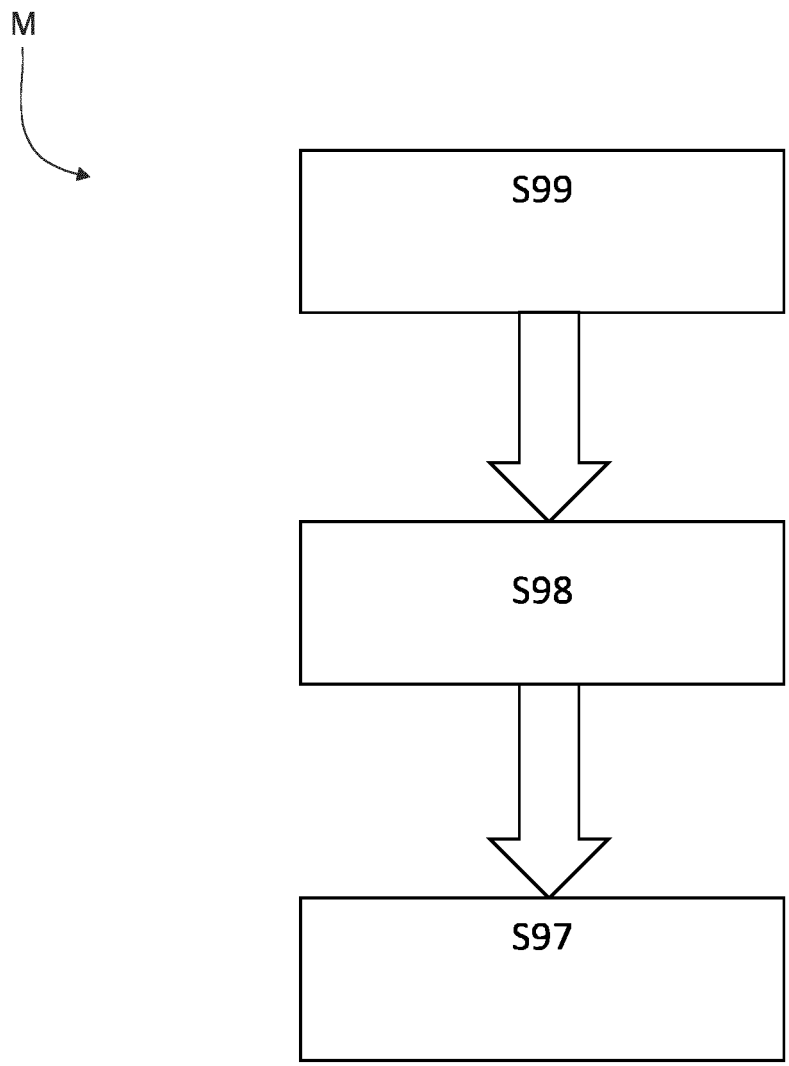
FIG. 8A shows basic steps of an example of a method for preparing a patient's sample before analysis.

FIG. 8A shows basic steps of an example of a method M for preparing a patient's sample before analysis, comprising the following steps:

a) receiving S99 a sample in a receiving chamber;
b) putting S98 a reagent in contact with the sample thus providing a liquid including the patient's sample and the reagent; and
c) supplying S97 the liquid to an analysis device for analysis purposes.

Figure 8B:
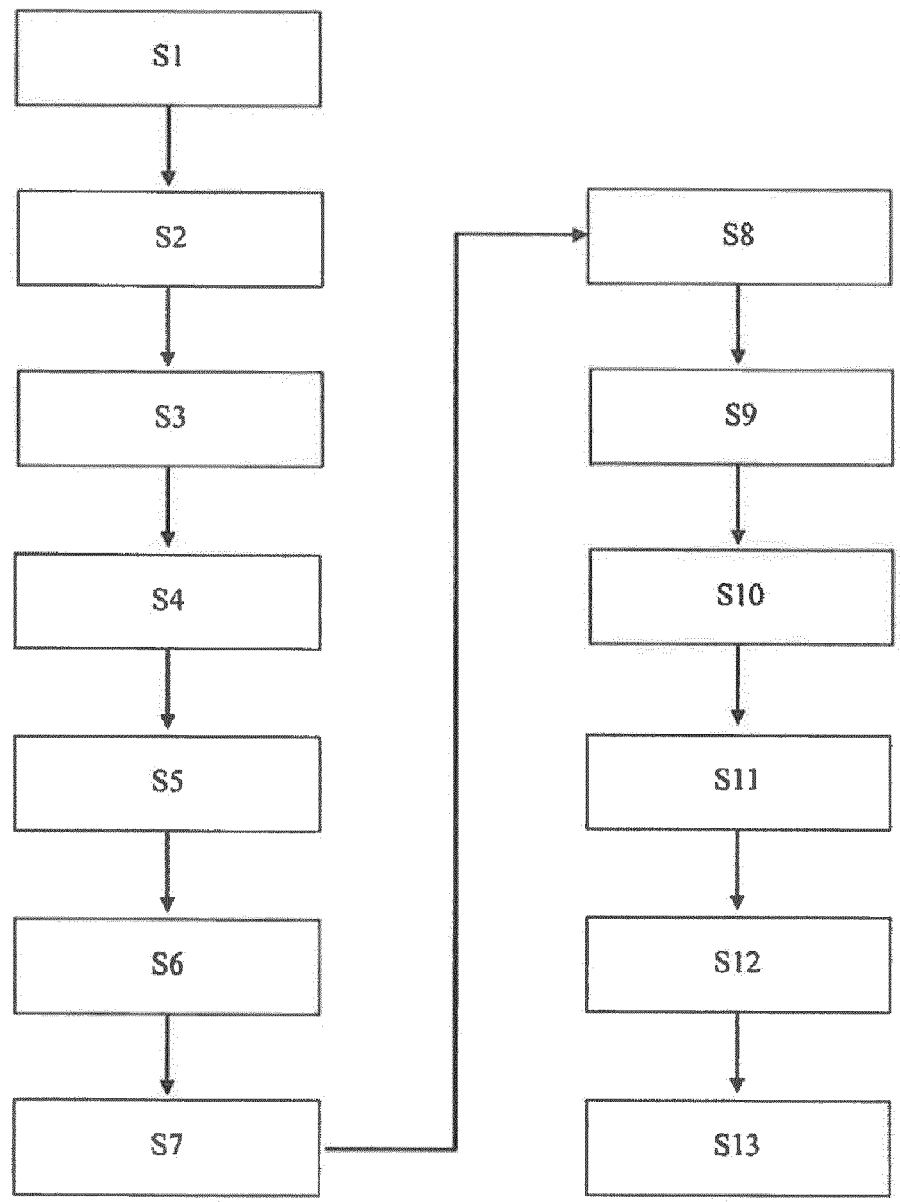
FIG. 8B is a flow chart illustrating steps of an example of a method for using the device.

FIG. 8B is a flowchart illustrating the principles of using a device as described above. It will be understood that the steps described with respect to the performed method are major steps, wherein these major steps might be differentiated or divided into several sub steps. Furthermore, there might be also sub steps between these major steps. A sub step is only mentioned if that step is important for the understanding of the principles of the method.

A method of using a container as described above may comprise the steps of providing a liquid or dry first reagent (S1) and inserting the first reagent into the first reagent reservoir (S2), receiving a patient's sample or at least a portion of a sample collecting element with such a sample in the receiving chamber (S3), cutting a portion of the sample collecting element which protrudes out of the receiving chamber (S4), closing the housing of the device (S5), sealing the receiving chamber (S6), supplying the first reagent to the patient's sample possibly at the sample collecting element (S7) so as to remove the patient's sample at least partially from the sample collecting element (S8) and to mix the patient's sample with the first reagent (S9). It is noted that for example step S4 may be omitted when the sample collecting element is short enough to fit completely into the receiving chamber. On the other hand, the first actuator may be configured so that steps S5 and S6 may be performed simultaneously. Further, it will be understood that the patient's sample may be removed from the sample collecting element by solving the sample in the liquid, i.e. step S9 may cause the step S8. It is in particular noted that all of steps S4 through S9 may be performed by one movement of the first actuator. In case of a liquid patient's sample, the first reagent may even be a dry reagent.

The following method steps may be performed by an actuation of the second actuator, starting from a condition in which a liquid including a patient's sample is already received in the receiving chamber of the housing, i.e. starting from step S9. A method may comprise the steps of extracting a predetermined amount of the liquid from the receiving chamber (S10), supplying the metered liquid to a reagent reservoir (S11), mixing the liquid with a reagent received in the reagent reservoir (S12), and generating a turbulent flow of the liquid (S13). The turbulent flow may be generated by a reduced channel diameter accelerating the fluid and/or by providing edges in the flow path.

Figure 9:
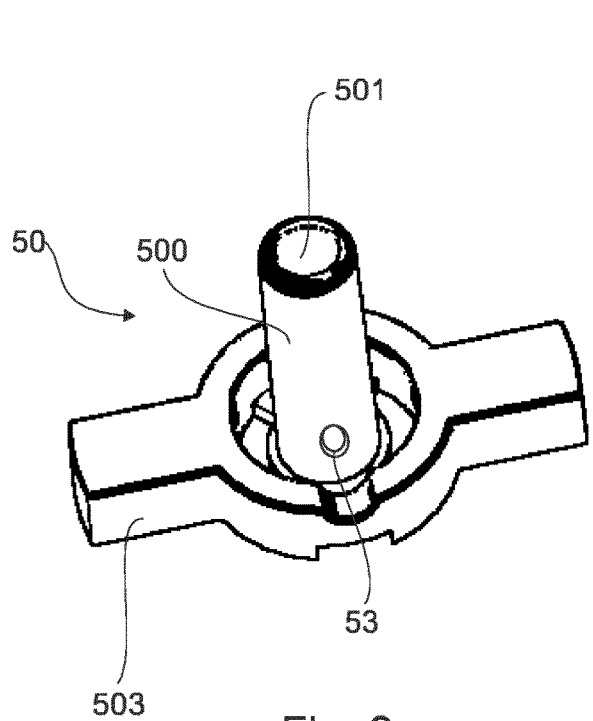
FIG. 9 illustrates in a perspective view a top end view of a second actuator.

FIG. 9 illustrates in a perspective view a top end view of the second actuator 500.

Figure 10:
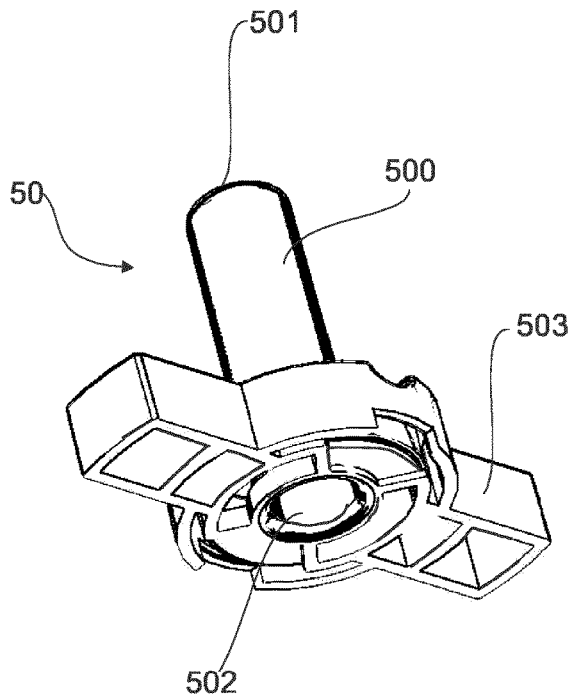
FIG. 10 illustrates in a perspective view a bottom end view of the second actuator.

FIG. 10 illustrates in a perspective view a bottom end view of the second actuator. As can be derived from FIGS. 9 and 10 the second actuator 50 comprises two handles or grip portions 503. The handles 503 are connected via a ring-shaped element and bars, protruding from the ring-shaped element at the outer surface of the cylinder 500. The cylinder 500 comprises a closed tope end 501 and an open bottom end 503. Adjacent to the open bottom end there is formed a suction opening 53 with is in fluid connection with the inner volume of the cylinder 500.

Figure 11:
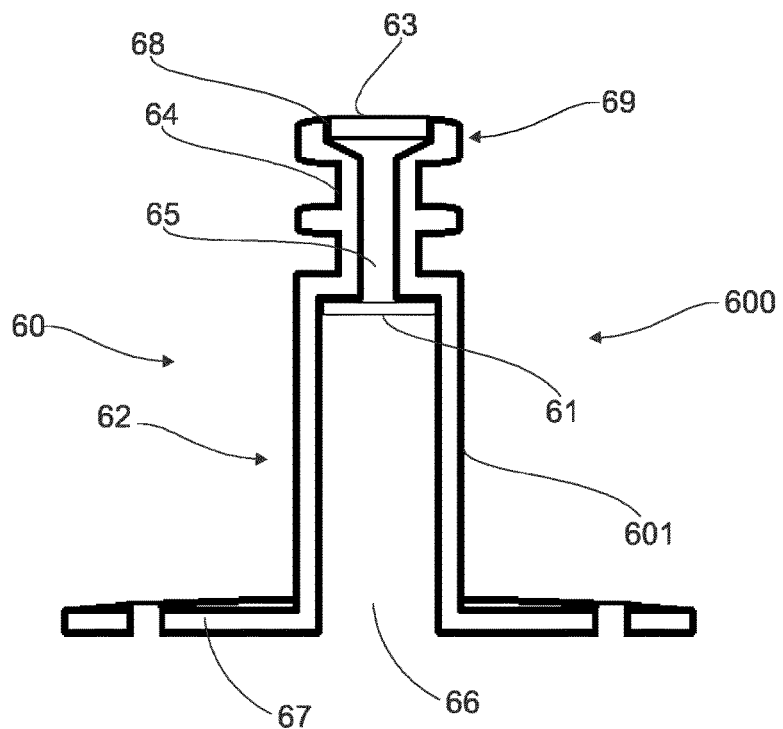
FIG. 11 illustrates in a section view of a connecting element movable supported within the second actuator for generating a metering chamber.

FIG. 11 illustrates in a section view of a connecting element movable supported within the second actuator for generating a metering chamber 52. The connection element 60 functions as a piston 600, including a receiving opening 68 for receiving a liquid and leading the same to a small tube opening to the second orifice 66 for delivering the liquid further to a reagent reservoir 82 of the base. In an example, the piston portion 62 is provided with a seal 51 for sealing the piston portion against the inner wall of the metering chamber 52 of the second actuator 50.

Furthermore, at the receiving opening 68 a filter element 63 is provided to filter some elements of the extracted liquid, the filter component being provided in the liquid path, between the receiving chamber 32 and the metering chamber.

Figures 12A, 12B:
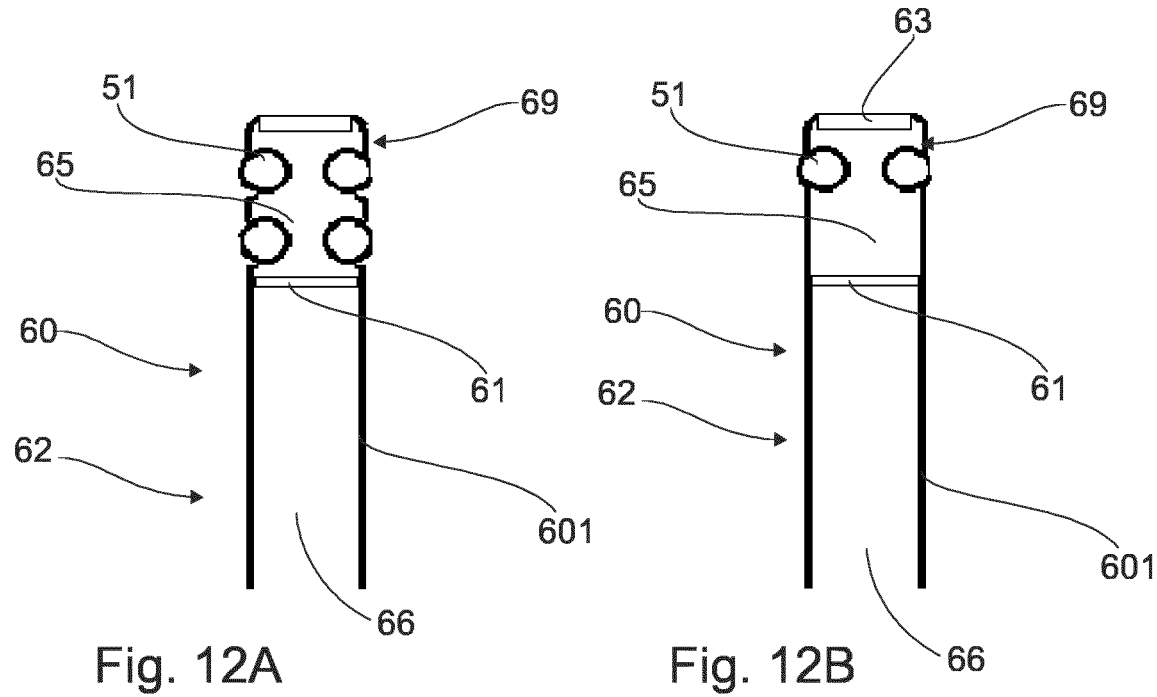
FIGS. 12A to 12D show embodiments of the connecting element.
Figures 12C, 12D:
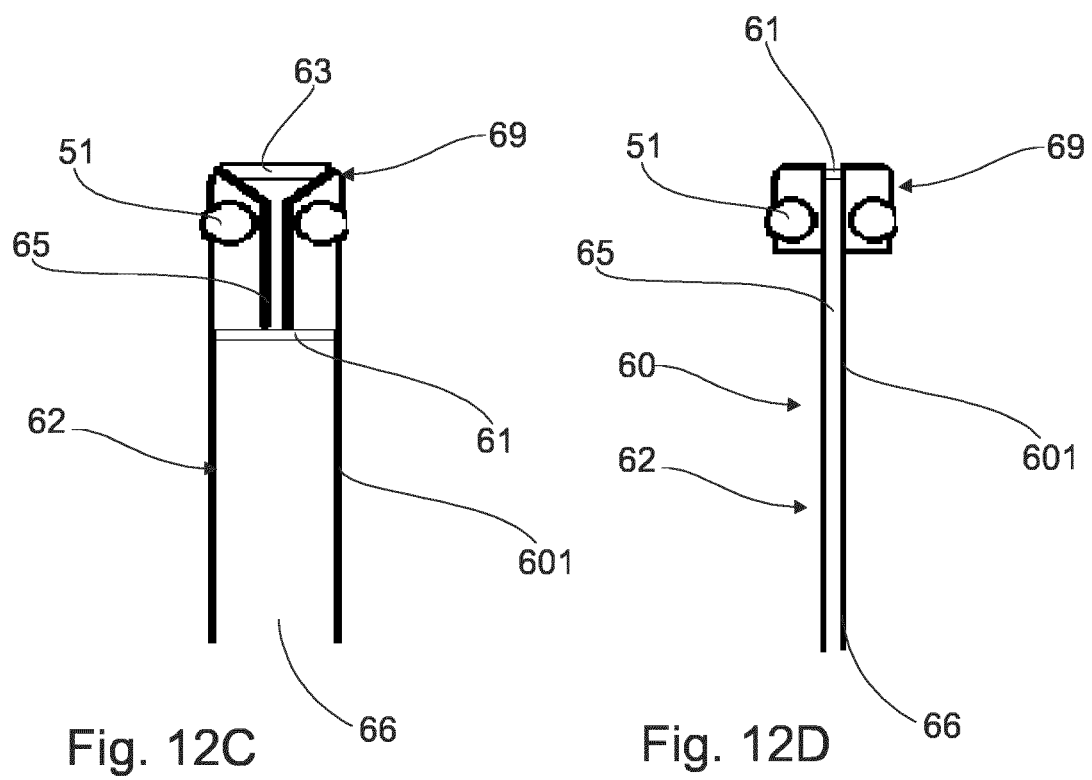

The receiving opening 68 can be formed like a funnel, like for example shown in the section vies of FIG. 11 and FIG. 12C. The filter element is only optional. In FIG. 12A to FIG. 12D different embodiments of the connection element 60 are shown, wherein each connection element 60 has different features of FIG. 11, wherein on FIG. 12D an embodiment of the connection element 60 is shown, having the minimum features, like a piston portion 69, a pierceable membrane 61, and a small tube 65, leading to a second orifice 66 for delivering the liquid to a regent reservoir 82 of the base. For example, according to FIG. 12C the small tube 65 of the piston portion 69 is provided with a sealing 61 at one end and with a filter 63 at the other end for maintaining a vacuum generated in the metering chamber.

Again, referring to FIG. 11, beneath the filter element 63 there is a support structure, which can be formed like a spoked-wheel (not show), for supporting the filter element 63. Beneath of the support element there is the funnel 68 which lead into a small tube 65. The small tube comprises at its lower end portion a membrane 61, which membrane 61 is put onto the opening of the small tube 65 as a sticker. This membrane 61 has the function to seal the interior cylinder 500 when a vacuum is generated. The membrane 61 must be damage or punctured for draining a liquid stored in the metering chamber 52 of the cylinder 500. Preferably, this is performed with the help of a hollow needle, like a cannula 72, shown for example in FIGS. 16 to 19 and in FIG. 20. The piston portion 69 is formed as interior cylinder and is provided with a filter element 63 through which the liquid has to pass to be deliver downwards.

The piston portion 69 of the connection portion 60 of FIG. 11 has a blocked through hole 65, which is blocked by the hermetic tight sealing 61 for maintaining the vacuum to be established within the metering chamber 52. The sealing 61 can be a pierceable fluid-tight membrane, which can be pierced by a needle or cannula 72. The pierceable membrane can be pierced by a cannula 72 to generate an opening 700 in the receiving chamber for draining a fluid collected in the receiving chamber.

Now referring to FIGS. 12A to 12D, which show different embodiments of the connection element 60 in section views, wherein the FIG. 12A show an embodiment of the connection element 60 which includes some relevant features, like the membrane 61, which should be liquid tight such that a vacuum and or liquid can be blocked to escape through the small tube 65, but also pierceable or breakable by the cannula for creating an opening in the membrane such that the seal of the small tube 65 is broken and the liquid can be evacuated through the small tube 65. FIGS. 12A to 12C show further embodiments of the connection element 60, wherein further components are added to the embodiment of the connection element, shown in FIG. 12D.

In an embodiment not shown the pierceable membrane 61 is replaced by a controllable valve which seals the small tube 65 when necessary and is opened when the liquid should be drained through the small tube. The valve can be actuated via signals or mechanical via the cannula.

Figure 17:
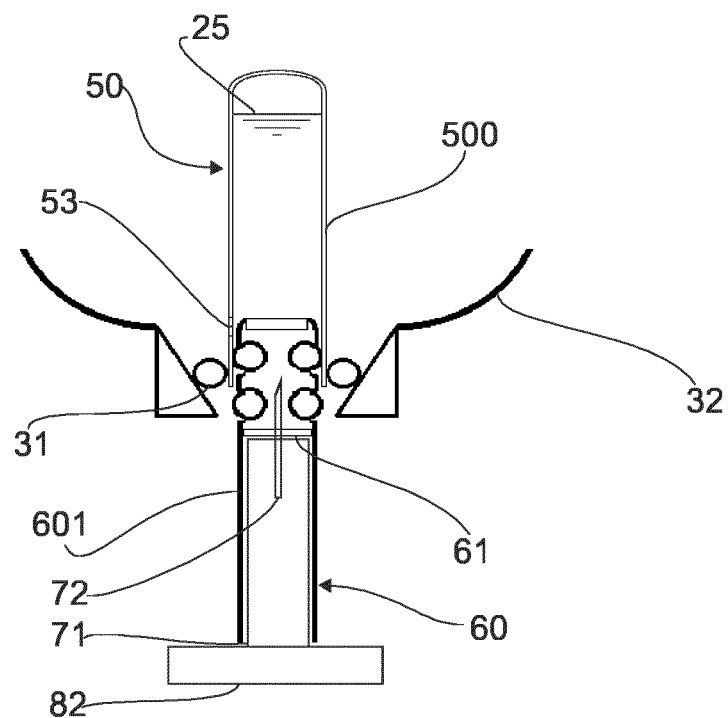
Figure 18:
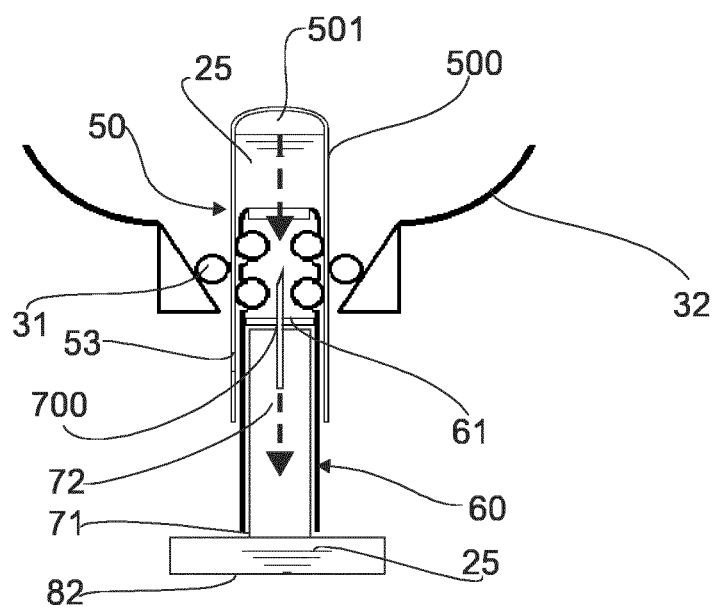
Figure 19:
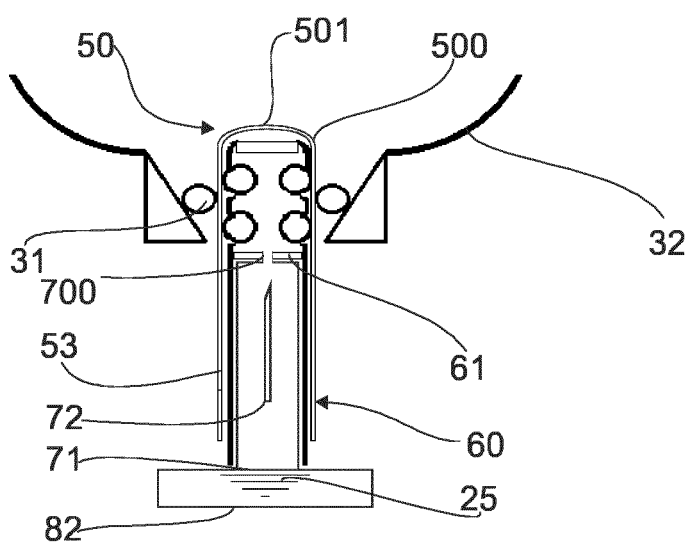

Preferably, as shown in FIGS. 17 and 18, the cannula 72 remains and extends during the drainage of the metering chamber in and through the membrane 61, such that the fluid is delivered via the cannula to the reagent reservoir 82 of the cartridge 200. In another embodiment, the sealing can be a valve, which can be actuated via signals or mechanical via the cannula. The metering chamber is drained first by piercing the pierceable membrane such that the tip of the cannula pierces through the pierceable membrane. The fluid in the metering chamber can then leak preferably trough a filter 63 provided in the connection element 60 or in another embodiment directly into the base. The filter 63 can be provided, but in another embodiment the filter can be omitted, depending on the used samples and/or reagents.

Figure 13:
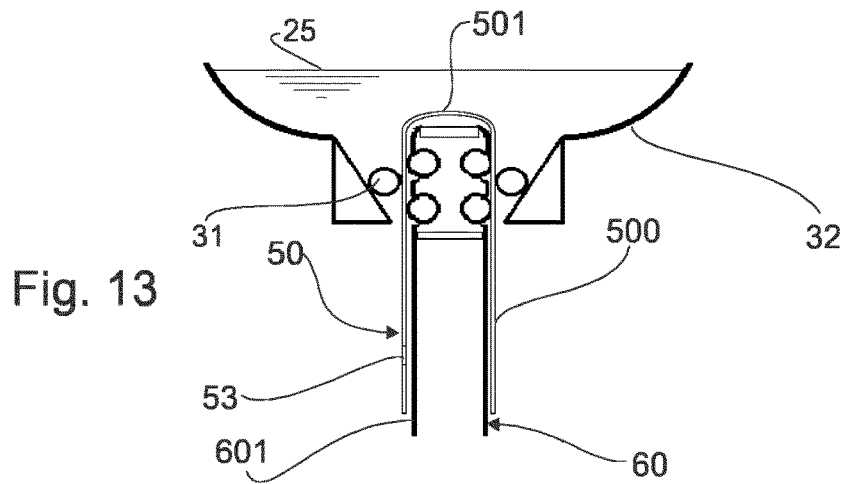
FIGS. 13 to 15 show the movement of the second actuator relative to the connection element shown in FIG. 11 for generating a vacuum in a metering chamber defined by the actuator.
Figure 14:
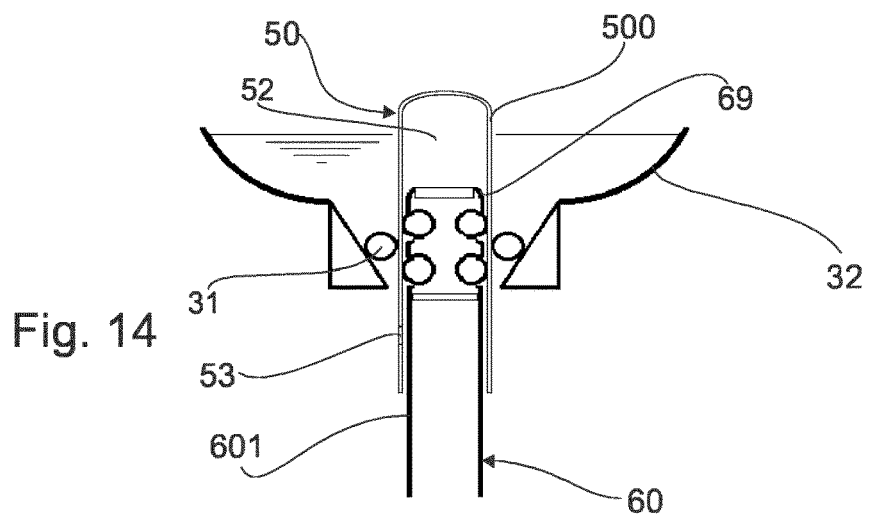
Figure 15:
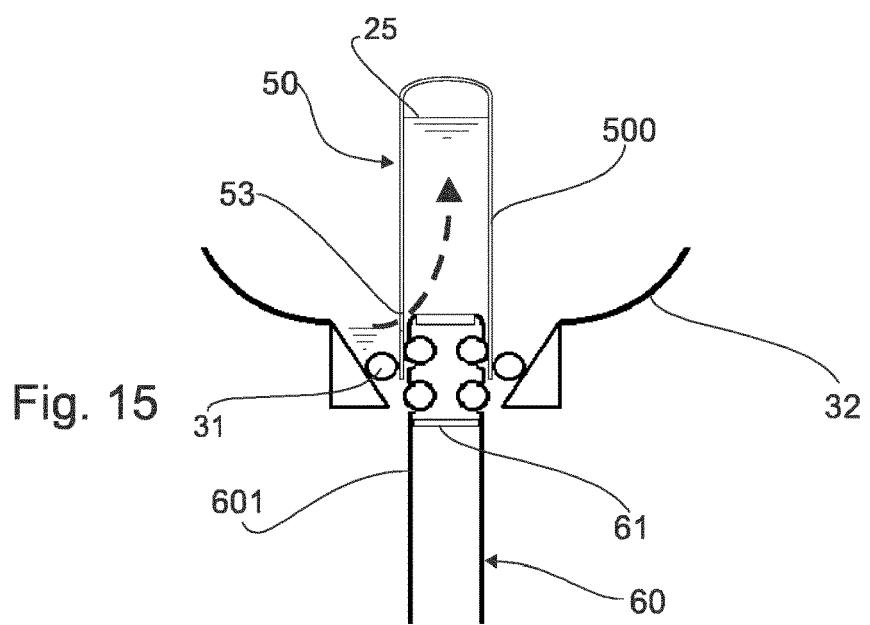

Now referring to FIGS. 13 to 15, which schematically illustrate the generation of a vacuum in the metering chamber. To achieve this, preferably the second actuator 50 is moved relative to the connection element 60. FIG. 13 illustrates a start position when connection element 60 is inserted within the hollow cylinder of the second actuator 50. FIG. 14 illustrates an intermediate position when the second actuator has partially moved away from the piston portion 69 and a vacuum is generated between the piston portion 69 of the connection element 60 and the closed top end portion of the second actuator 20. FIG. 15 illustrates a reversible end position of the second actuator 50 and the state when the suction opening 53 is aligned to establish connection between the metering chamber 52 and the receiving chamber 32 when the liquid is sucked into the metering chamber 52.

With reference to FIGS. 9, 10, 11 and 13 to 15, the metering actuator 50 comprises a cylindrical body 500 defining a metering lumen 52 with the closed top end 501 and the open bottom end 502. Furthermore, the cylindrical body 500 comprises adjacent to the open bottom end 502 in a lateral side wall of the cylindrical body 500 the suction opening 53. The axis of the suction opening 53 is substantially perpendicular to the extending axis between the closed top end 501 and the open bottom end 502 of the cylindrical body 500. The open end 501 is for receiving the piston 600, which can be liquid-tight moved within the lumen of the cylindrical body 500. The cylindrical body 500 is relative movable to the position 600. Preferably, the cylindrical body 500 is moved and the piston 600 remains stationary.

When the cylindrical body 500 and the piston 600 are moved with respect to each other, a reduced pressure, preferable a vacuum (=negative pressure) is generated, since the volume between the closed top end 501 of the cylindrical body 500 and the piston portion 69 of the piston 600 facing to the closed end 501 increases. The cylindrical body 500 and/or the piston 600 are movable between a top dead center or starting position shown in FIG. 13, in which the top end portion 501 of the cylindrical body 500 and the end portion of the piston portion 69 are close to each other (starting position), and the suction opening is blocked, and an bottom dead center or end position, shown in FIG. 15, in which the top end portion of the cylindrical body 500 and the piston portion 69 are distanced to each other, and the suction opening 53 is unblocked, such that a liquid sample 25 can be sucked into the lumen 52 of the cylindrical body 500.

According to an exemplary embodiment of the system the following method steps can be executed, for metering a liquid of the receiving chamber into the metering chamber:
  providing a liquid or dry first reagent 25 (SI),
  inserting the first reagent 25 into the first reagent reservoir 24 (SII),
  inserting a cotton swab 400 into a receiving opening 14 (SIII).
In a further example, it is provided:
  moving a first and a second handle 16, 22 towards each other, in particular in a rotational movement for holding and handling the device in one hand, like for example shown in FIG. 5. But the movement can be also performed as a translational movement, like a linear, curved movement.

In further not always necessary sub steps i) to iii), when the cotton swab includes a wooden or plastic a rod:
i) the rod can be or must be cut, in particular when the rod protrudes out of the receiving opening;
ii) then, when the rod has been cut, the receiving chamber 32 can be closed.

Most cotton swabs are provided with a predetermined breaking point. But usually the rod is often too long/and or the predetermined breaking point is at the wrong position relative to the closing element of the device, i.e. the predetermined breaking point is lower or higher as the location of the closing element of the device. Then it can be necessary that the rod must be cut. The device according to the invention has due to its overall compact receiving chamber very small dimension compared to a conventional cotton swab. Thus, a cutting of the cotton swab might be necessary.

But with the device according to the invention other devices for taking a sample can be used, which would fit into the opening 14 and in the volume defined by the receiving chamber 32, like a swamp. Then a cutting of the sample is not necessary, thus the cutting step is not obligatory and always necessary.

When the receiving open 14 is closed, the two handles are brought in contact with each other, as for example shown in FIG. 5 from step A to step B and can be clamped together in step D by means of a clamping mechanism to omit unwanted reopening of the receiving chamber 32.

In step C to step D of the movement of the handles 16, 22 the relevant translational or rotational displacement within the receiving chamber 32 takes place such that a small clearance is closed. In this small clearance, there is a bag of liquid or the reagent 25 in liquid form. The bag of liquid is opened and squeezed by the last displacement.

Thus, a third step is:
iii) releasing of the provided liquid (SIV).

When the fluid comes in contact with the cotton swab 400 and absorbs for example the virus or virus particles contained on the cotton swab 400, it is an aim of the invention to discharge a predetermined, exact volume of the liquid with the absorbed virus or virus particles for further analysis steps, for example in the analysis device 300.

To achieve this the container 100 with the closed handles 16, 22 is mounted/snapped onto the interface element 70 of the cartridge 200 (SV). By mounting/snapping the container onto the cartridge a negative pressure can be generated in a volume for sucking the fluid into the volume.

To achieve this, the outer cylinder 500 of the second actuator 50 is moved relative to the piston 600 (SVI) as shown in FIGS. 13 to 15.

The piston 600, shown in FIG. 11. can be formed as interior cylinder 601 located within the outer cylinder 600. A first seal 51 (O-ring) is positioned between the outer cylinder 500 and the interior cylinder 601. A second seal 31 (O-ring) is positioned between the outer cylinder 500 and the region, in which the liquid is stored. An orifice 53 is provided at the lower end portion of the outer cylinder 500, which orifice is at first not sealed. The piston is formed as interior cylinder 601 and is provided with a filter element through which the liquid has to pass to be deliver downwards.

When outer cylinder 600 is moved upwards from the starting position shown in FIG. 13—towards the direction where the cotton swamp is inserted—at the same time the orifice 53 is moved up, as shown in FIG. 14, in an intermediate position.

At an upper end portion of the receiving chamber 32, the orifice 53 passes the first seal 51 of the interior cylinder, in the embodiment shown two O-rings. Thereafter, when having passed the two-O-rings 51, the orifice 53 is in contact with a generated volume created between the outer cylinder 500 and the interior cylinder 601, and makes contact with the fluid 25 in the receiving chamber, as shown in FIG. 15. With the generated volume V2, a vacuum is generated with which liquid is sucked into the volume of the outer cylinder 500 and the interior cylinder 601, as indicated with the dotted arrow in FIG. 15.

By moving the outer cylinder 500 the volume is created into which the liquid is sucked.

For generating the vacuum V2, the inner cylinder 601 is provided with lateral arms 503 which are mounted on a rim 702 of the interface element 70 of a basis module of the cartridge 202. By moving the hand-operated container 100 downwards the arms 503 are moved relative to the hand-operated container upwards, since the arms stay on the rim 702 and the container is pushed down into cylindrical receiving groove, formed complementary to the outer dimensions of the lower, second housing part 30 of the container 100.

In a further example, a container 100 of a device for metering a patient's sample before analysis is provided. The container 100 comprises: a receiving chamber 32 for receiving a liquid 25 of a sample; and an actuator 50 comprising a cylindrical metering chamber 52 for metering the fluid sample 25 defined by a closed top end 501 and an open bottom end 502 both connected by a circumferential wall 500.

Between the top end 501 and the bottom end 502 in the circumferential wall the suction opening 53 is provided, which allows a fluid connection with the metering chamber 52 of the actuator 50 and the receiving chamber 32. The connection element 60 comprises a piston portion 69 with a through hole 65 closed by the sealing 61.

The piston portion 69 is moveable supported within the metering chamber 52 of the actuator 50 between a bottom dead position, in which the suction opening is blocked and the piston portion is adjacent to the closed end, and a top dead position, in which the suction opening is unblocked and brought in fluid connection with the receiving chamber.

Figure 20:
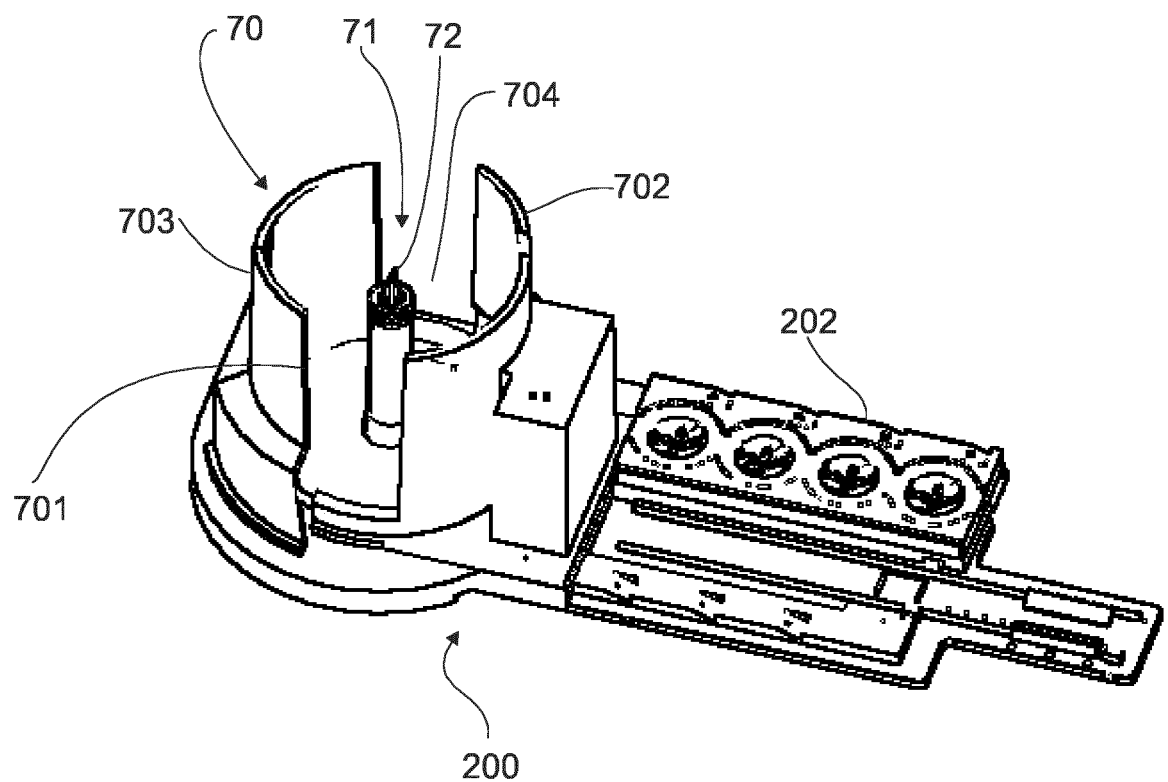
FIG. 20 illustrates in detail a base with which the container can be coupled.

When moving the piston portion 69 and the metering chamber 52 relative to each other from the top dead position into the bottom dead position, a volume, which increases between the closed top end and the piston portion, and a vacuum negative pressure is generated, such that the liquid, stored in the receiving chamber 32, can be sucked into the metering chamber, when the opening 53 is moved in fluid-connection with the receiving chamber Referring now to FIG. 20, which shows in detail the base with which the container can be coupled to perform the above-mentioned steps SI to SVI.

In FIG. 20 the interface element 70 is illustrated in a perspective view, wherein the cannula 72 of the piercing element 71 is in its extended position. In the extended position, the tip of the cannula 72 protrudes out of the cylindrical body of the piercing element 71 to at least pierce the pierceable membrane 61 of the connection element 60.

In an example, the container 100, in particular the handle 501 of the actuator 50, is engageable onto the outer rim 702 of the interface element 70 and can lower part of the housing o the container can at least partially be engaged into the receiving groove 702 of the interface element 70 of the base.

The pierceable membrane 61 is configured to seal a generated vacuum in the lumen of the metering chamber 52, when the second actuator is in the end position. The pierceable membrane 61 is pierceable by the cannula for releasing the liquid sucked into the metering chamber. The cannula or the needle is a part of the cartridge, and is movable between a retract position, in which the tip of the cannula is provide within the piercing element 71, and an extended position in which the tip of the cannula 72 protrudes out of the piercing element for piercing the pierceable membrane. In FIG. 20 the cannula 72 is shown in the extended position for piercing the pierceable membrane 61.

FIGS. 16 to 19 illustrate the steps for supplying the liquid from the metering chamber 25 to a receiving volume, as for example the second reagent reservoir 82 of the base. The next steps shown in FIGS. 16 to 19 have the purpose to deliver the liquid to the cartridge or carrier 202 used for the analysis steps.

Figure 16:
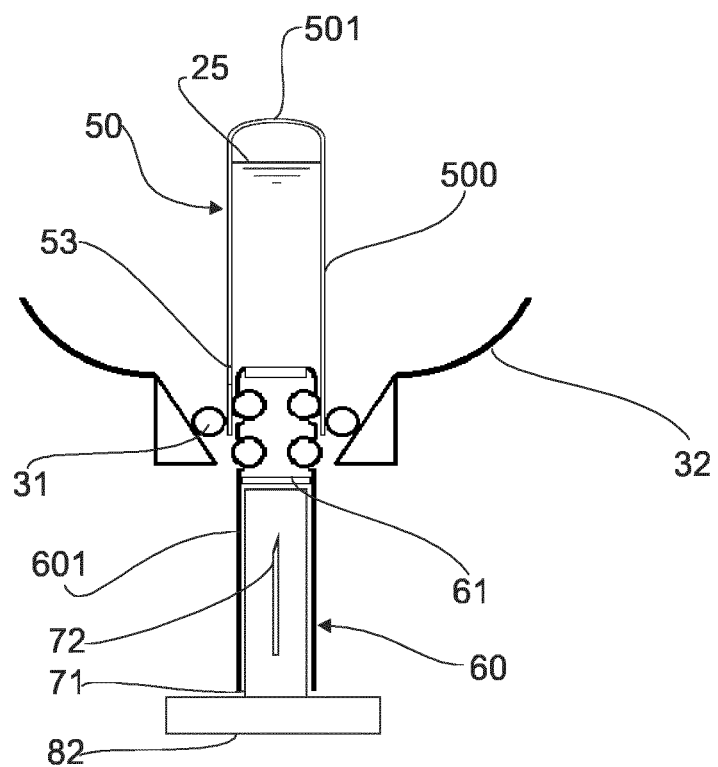
FIG. 16 illustrates the state when the through hole is aligned to establish connection between the metering chamber and the receiving chamber when the liquid is sucked into the metering chamber.

FIG. 16 shows the second actuator 50 in its end position, in which the fluid of the receiving chamber 32 has been sucked into the metering chamber 52, define by the inner lumen of the cylinder of the second actuator 50 and the piston portion 69 of the connection portion. Furthermore, the container 10 including the second actuator 50 and the connection element 60 with its piston portion, has been coupled with the interface element 70, such that the second lower housing part 30 of the container 10 is at least partially inserted into the receiving groove 702 and a piercing element 71 of a cartridge 200 is inserted into the connection element 60, wherein the handles 503 of the second actuator 50 remains above the receiving groove 702, and are engaged on the rim 702 of the interface element 70.

The connection element 60 comprises an interior cylinder 601 into which the piercing element 71 is insertable for puncturing the pierceable member.

Preferably, the container 100 is inserted into the receiving groove 704, when the actuator, in particular the handle, is in the starting position, i.e. there is a reagent liquid 25 in the receiving chamber 32 of the container, but the content is not yet provided in the metering chamber of the actuator.

The container is inserted with its lower, second housing part 30 into the receiving groove 704, but the handle of the actuator 50 is engaged onto the rim 702 of the circumferential wall of the interface element 70. Then, the container 100 is forced down such that the lower, second housing part is inserted in the receiving groove 704, but the handles 503 remains on the outer rim 702. The handle 503 actuates the actuator 50 such that the actuator 50 is moved with respect of the piston portion 69 of the connection element 62, generating a negative pressure and an increasing volume forming the metering chamber. When the suction opening is aligned with the receiving chamber, the liquid content is sucked into the metering chamber 52 due to the vacuum generated in the metering chamber.

The membrane 61 must be damage or punctured for draining the metered liquid contained in the metering chamber 52. Preferably, this is performed with the help of a hollow needle, like a cannula 72. In FIG. 16, the cannula 72 is shown in a safe, and retracted position, such that the piercing tip cannot damage the pierceable membrane 61

The puncturing of the membrane 61 is performed after the vacuum is generated, the liquid is collected in the metering chamber 52 and the container is mounted on the base. Before the membrane 61 is pierced the hand-operated container 100 and the base-module are locked against each other by inserting the piercing element 71 of the base into the connection element 62 as described above. This condition is partially shown in FIG. 16, without the handles 501 of the second actuator and the base plate 67 of the connection element 60. The hollow needle or cannula 72 is hide and secured in the piercing cylinder of the piercing element 71 to omit the risk of injuries and contamination. The piercing cylinder is dimensioned for receiving the interior cylinder 601 of the connection element 60.

Before the actuator 50 is moved back in its starting position the cannula 72 is activated for piercing the pierceable membrane 61, as for example shown in FIG. 17. The cannula 72 is shown in FIG. 17 in its extracted position. For moving the actuator 50 downwards in the starting position shown in FIG. 19, the arms 503 have to be inserted in the sideward slots or lateral recesses 701, such that that the handles or arms 503 of the actuator 50 can be moved downwards.

By turning the hand-operated container 100 around the base module by approximately 20° degree, the lateral arms 503 are simultaneously rotated, such that they are move from the upper rim 702 to the lateral recesses 701 to be moved in theses recesses 701 downwards with the help of the gravity and manual operation, or optional by the force of a spring. Since the upper face of the upper rim 702 includes an inclination, a first downward setting of the arms 503 and therefore of the outer cylinder 500 is performed. Preferably, during this first downward setting the membrane 61 is puncture by the hollow needle 72.

In the step shown in FIG. 18 the outer cylinder 500 is moved downwards for emptying the metered volume V2 of the liquid in the generated volume. When the orifice 53 passed the O-ring 31, initially a little portion of the liquid is forced back to the receiving chamber 32.

By moving the arms 503 downwards in the recesses 701 the metered volume V2 is drained and delivered to the cartridge, in particular to the second reagent reservoir 82, or to a liquid receiving volume of another device. Optional there are devices for generating a turbulent flow in the meted volume V2 when delivered to the cartridge for improving the mixing of the reagent and the sample. The device for generating a turbulent flow can be provided in the small tube or at the second orifice of the connection portion, or at an entrance of the second reagent reservoir 82.

In a further example, a method of using a container 100 as described above is provided. The method comprises the steps of:

providing a reagent and/or a liquid in the receiving chamber 32 of the housing 10 of the container;

inserting a sample collecting element 400 into the receiving opening 14 of the device;

actuating a first actuator 20 comprising a first handle 16 and a second handle 22 by moving the same relative to each other for closing the receiving opening 1, wherein the relative movement cause an in contact-bringing of a reagent stored in a first reagent reservoir 24 of the device with the sample collection element 400;

extracting a predetermined amount of the liquid from the receiving chamber into a metering chamber, by actuation a second actuator 50 to generate a volume; and extracting the predetermined amount in the metering chamber to a liquid receiving volume of e.g. a cartridge by actuating the second actuator by decreasing the volume.

In a further example, the method further comprises the steps of cutting a bar or stem of the sample collecting element 400 during the closing of the receiving opening 14 by means of a cutting element in a cutting opening 15 of the container 100.

The sample collecting element 400 can be, for example, a cotton swab with a bar. The bar can be cut by a cutting element, when the bar is too long and protrudes out of the receiving opening of the device. But there some cotton swabs comprise a predetermined braking point. This method step is optional, since the sample collecting element is not restricted to a cotton swab with a bar. For example, the sample collecting element 400 can be a cotton swab which fits completely into the receiving chamber, wherein it is not necessary to cut the stamp.

In a further example, the method further comprises the steps of squeezing a reagent into the receiving chamber, by further actuating the first and second handle until both are in contact with each other.

In a reagent reservoir, a reagent bag 25 is provided in a space. For releasing the reagent, the reagent bag is compressed till the bag ruptures by minimizing the receiving space of the reagent bag. The handles are configured such that when rotating the same together, the receiving space is minimized and the content of the reagent bag is squeezed out. The bag can be provided with predetermined rupture points, which ease the rupture of the reagent bag. In another embodiment, cutting elements are provided for opening the reagent bag and for releasing the reagent in the bag by cutting into the bag. In both cases the reagent is squeezed out since the space in which the bag is contained is minimized by actuating the handles. The reagent can be a liquid or a solid. When the reagent is a solid, a second bag can be provided which contains a liquid for providing a solution of the solid reagent and the liquid for solve the elements containing in the sample collecting element.

In a further example, the method further comprises the steps of locking the first and second handle by means of a clamping device.

The reagent should react and or solve the elements contained in the sample collecting element 400. For omitting any further manipulation of the device, the handles can be provided with a lock or clamp mechanisms. The clamp mechanism can be activated by the user or can be configured such that when the handles are brought in contact with each other the clamp mechanism is activated. The clamp mechanism should prevent an ex post opening of the handles to omit a manipulation of the content of the receiving chamber, to prevent a contamination of the receiving chamber with elements of the environment, and to protect the user against the content of the receiving chamber.

In a further example, the method further comprises removing a predetermined amount of the fluid contained in the receiving chamber by sucking the predetermined amount into a generated volume in the second actuator 50, wherein the generated volume is generated by increasing the distance of a top end portion 501 of the second actuator 50 and a position portion 600 of the connection portion 60.

In a further example, the method further comprises moving the second actuator into engagement with the receiving groove 704 such that the actuator can be moved towards the cartridge, wherein a cannula 72 in the piercing element 71 is moved into an extending position for piercing the pierceable membrane 61.

When the suction of the liquid is terminated, the handle of the actuator is rotated to fit into the handle receiving groove 704 of the interface element 70. The handle of the actuator is now pushed in the direction of the bottom of the interface element. By doing this, the pierceable membrane is pierced with or just before by the cannula of the piercing element. The cannula 72 must be activated to pierce the pierceable membrane. This can be performed by a trigger to be pushed by the user or a sensor which can recognize when the handle of the actuator is inserted into the dandle receiving groove 704.

In a further example, the method further comprises pushing the actuator back such that the piston portion is returned into a top dead position, wherein the fluid in the metering chamber is pushed through the pierced sealing 71 into a reagent reservoir of the cartridge 200.

After the sealing, i.e. the pierceable membrane 61, is pierced by the cannula 72, the handle of the actuator is pushed downwards. This causes a transfer of the liquid from the metering chamber to a reagent reservoir 82 in the cartridge 200. The closed top end of the metering chamber forces the liquid in the metering chamber at least partial through the filter and into and through the lumen of cannula and into the reagent reservoir 82 of the cartridge. When the metering chamber is empty, normally when the handle of the actuator has reached the bottom of the receiving groove, the cannula is retraced, the container is disengaged from the receiving groove, and the sample in the reagent reservoir can be analyzed by the analysis device 300. The container can then be disposed, if the container is intended for a single use only.

The connection element 60 provides a hollow space 66 into which the piercing element is insert able for puncturing the pierceable member. Preferably, the container is inserted into the receiving groove 704 when the actuator is, in particular the handle, in the starting position, i.e. there is a suspension 25 in the receiving chamber of the container, but the content is not jet provided in the metering chamber of the actuator. The container is inserted with its lower, second housing part 30 into the receiving groove 704 but the handle of the actuator 50 is engage onto the rim 702 of the circumferential wall of the interface element 70. Then the container is forced down such that the lower, second housing part is inserted in the receiving groove 704, but the handle 500 remains on the outer rim. The handle actuates the actuator such that the actuator 50 is moved with respect to the piston portion of the connection element, generating a negative pressure and an increasing volume in the metering chamber. When the suction opening reaches the receiving chamber containing the reagent 25, the liquid content is sucked into the metering chamber due to the generated vacuum. When the suction of the liquid is terminated, the handle of the actuator is rotated to fit into the handle receiving groove 704 of the interface element 70. The handle of the actuator is now pushed in direction to the bottom of the interface element. By doing this, the pierceable membrane is pierced with or just before by the cannula of the piercing element. The cannula must be activated to pierce the pierceable membrane. This can be performed by a trigger to be pushed by the user or a sensor which can recognize when the handle of the actuator is inserted into the handle receiving groove 701. After the cannula is pierced, the handle is pushed downwards. This causes a transfer of the liquid in the metering chamber to a reagent reservoir in the cartridge 200. The closed top end of the metering chamber forces the liquid in the metering chamber at least partial through the filter and into and through the cannula into the reagent reservoir of the cartridge. When the metering chamber is empty, normal when the handle of the actuator has reached the bottom of the receiving groove, the cannula is retraced, the container is disengaged from the receiving groove, and the sample in the reagent reservoir can be analyzed by the analysis device 300. The container can then be disposed, since the container is intended for a single use only.

Usually the sample preparation comprises the step of putting in contact a reactant with the sample, which e.g. specifically binds the analytes with said magnetic particles or chemically and/or mechanically interact with the cells of the sample for lysis purpose.

These FIGS. 13 to 19 further illustrates the difference to a syringe. In a syringe the receiving opening and the supplying opening are the same. In contrast thereto, according to the device the actuator comprises a first orifice 53 through which the liquid is received, and the connection element 60 defines a second opening, for example the opening 700 in the pierceable membrane 61, through which the metered fluid in the metering chamber is supplied to a second reagent reservoir 82 in the base 200.

Figure 21:
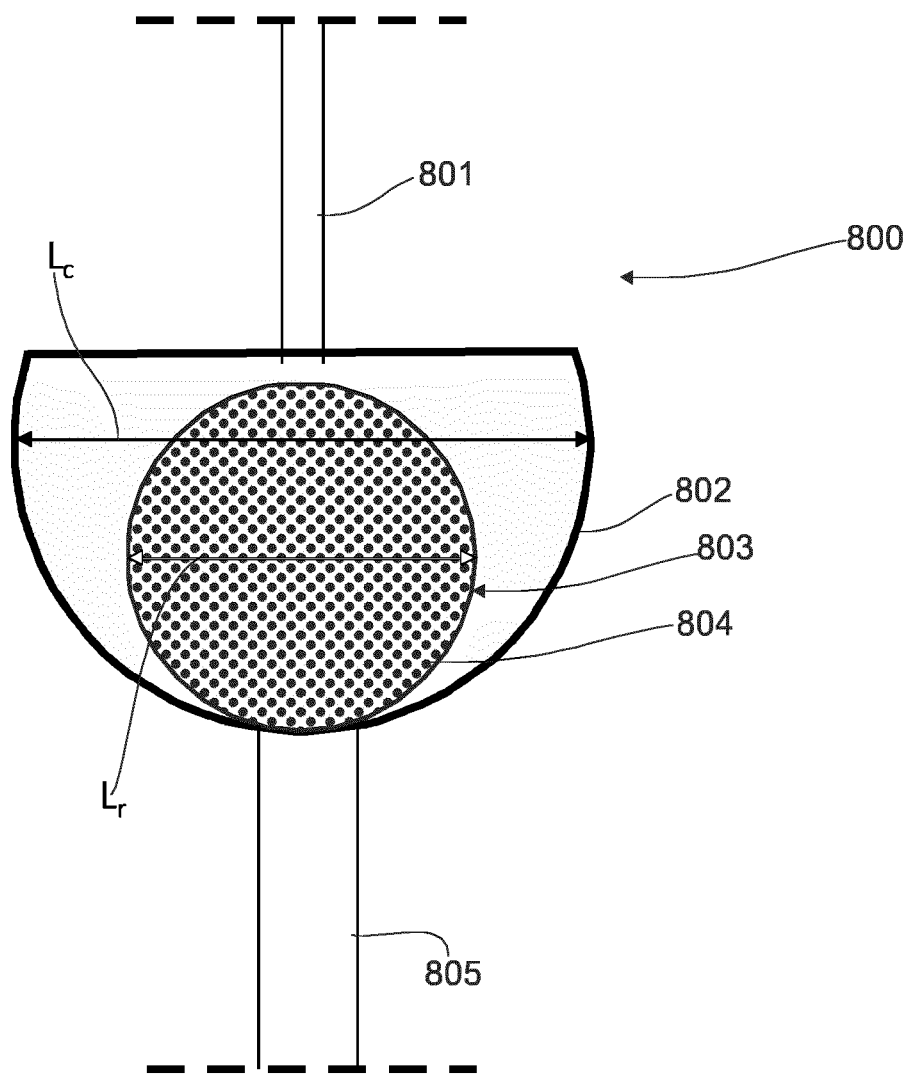
FIG. 21 illustrates in a section view a device for generating a turbulent flow.

Referring now to FIG. 21, which shows a device with which a turbulent flow can be generated when delivering the liquid from the metering chamber 52 to the reagent reservoir 82.

FIG. 21 illustrates in a schematic sectional view a turbulent flow generating device 800. The turbulent flow generating device works according to the principal that a liquid is delivered to a dry reagent 101, preferable a dehydrated reagent which contains magnetic particles 102. According to the invention the magnetic particles are to be bond to the analyte (liquid) after the preparation of the sample.

In a last step, the liquid may be passed through a gDNA filter and forced into turbulent contact with dried magnetic particles 804 that, once suspended, capture RNA molecules from the sample volume. These particles may then be collected by a magnet to undergo further processing, for example in the analysis device 300.

The characteristic dimension $L_c$ of the second reagent chamber 802 should be not much larger than the diameter $L_r$ of the body dried reagent 803 (typically a lyophilized sphere) for generating a turbulent flow when the liquid reaches the reagent, when the pierceable membrane 61 is pierced for draining the liquid in the metering chamber 52.

The relation according to the equation between a diameter $L_r$ of the reagent body 88 and a diameter $L_c$ of the second reagent chamber 802 can be calculated according to the following equation (I):

$$L_c < m * L_r;$$ (I)

wherein $L_r$=max. diameter of the dehydrated second reagent body 803; and $L_c$=max. inner width of the second reagent chamber 802; and m=multiplier, relation.

According to a preferred embodiment of the invention the multiplier m can be in the range from 1 to 5, preferably on the range 1.5 to 2, and most preferable m=2.

As shown in FIG. 21 the turbulent flow generating device 800 comprises an acceleration tube 801 with a constriction in the delivering tube, which supplies the liquid from the metering chamber 52 to the reagent reservoir 82 of the base, similar to a contraction choke (Venturi nozzle). The liquid from the metering chamber is introduced with a relative high flow speed due to the acceleration tube to the second reagent chamber 802 containing a second reagent 803 with magnetic particles 804. To ensure a good mixing of the liquid with the reagent 803 a turbulent flow should be generated. The maximum turbulence can be achieved when the relation between the diameter of the reagent body 803 and the inner width of the second reagent chamber 802 is relative small. Preferably the relation m between the max. diameter $L_r$ of the dehydrated second reagent body 803 and the max. inner width $L_c$ of the second reagent chamber 802 is in the range of m=1 to 5.

The second reagent chamber 802 includes an outlet, via which the mixture of liquid and reagent ca be delivered further to a vessel or volume of the analysis delivered for further analysis.

Also, the following examples are provided, which are numbered for easier reference:

1. A device for preparing a patient's sample before analysis, comprising: a housing, and an actuator. The housing includes a receiving chamber and a reagent reservoir. The receiving chamber is configured for receiving a liquid and the reagent reservoir is configured for receiving a reagent. The actuator is movable relative to the housing and is configured for extracting a predetermined amount of the liquid received in the receiving chamber and supplying the extracted liquid to the reagent reservoir, so that the reagent is suspended in the liquid.
2. The device of example 1, wherein the actuator comprises a metering chamber configured for receiving the predetermined amount of the liquid.
3. The device of example 2, wherein the actuator is further configured to generate a turbulent flow of the liquid, when supplying the liquid to the reagent reservoir.
4. The device of example 2 or 3, wherein the metering chamber comprises a first orifice through which the liquid is extracted from the receiving chamber to the metering chamber, and a second orifice through which the extracted liquid is supplied to the reagent reservoir.
5. The device of any of examples 2 to 4, wherein said extraction and/or said supply is (are) performed by suction, by creating a positive difference of pressure between: the receiving chamber and the metering chamber and/or between the metering chamber and the reagent reservoir.
6. The device of any of examples 1 to 5, wherein the actuation of the actuator is performed along a longitudinal axis of the housing.
7. The device of any one of examples 1 to 6, further comprising a pierceable membrane being configured to prevent the supplying of the liquid to the reagent reservoir.
8. The device of any one of examples 1 to 7, wherein the liquid includes lysed cells.
9. The device of any one of examples 1 to 8, wherein the reagent is a dried or solid reagent, preferably a magnetic reagent.
10. The device of any one of examples 1 to 8, further comprising a filtering component arranged to filter some elements of the extracted liquid, the filter component being provided in the liquid path, between the receiving chamber and an analysis device, and wherein the actuator being arranged such that the transfer of extracted liquid from the receiving chamber goes through the filter when the actuator is actuated.
11. A method of using a device according to example 1, comprising the steps of: receiving a liquid in the receiving chamber of the housing; extracting a predetermined amount of the liquid from the receiving chamber; supplying the metered liquid to a reagent reservoir; and mixing the liquid with a reagent received in the reagent reservoir. All these steps are implemented by actuating an actuator in a single operation.
12. The method of example 11, wherein the step of supplying the metered liquid to the reagent reservoir includes generating a turbulent flow of the liquid.
13. The method of any one of examples 11 and 12, further comprising the steps of receiving a patient's sample in the receiving chamber, wherein the step of receiving the liquid in the receiving chamber includes the step of applying the liquid to the patient's sample to solve the patient's sample in the liquid.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or. steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 first housing part
11 closing element
12 seal
13 cutting element
14 receiving opening
15 cutting opening
16 first handle
20 first actuator
21 seal
22 second handle, gripping member, lever member
23 supplying element
24 first reagent reservoir, reagent storage
25 reagent
30 second housing part
31 seal
32 receiving chamber (receiving space)
40 guiding element
50 second actuator
51 seal
52 metering chamber, lumen (metering space)
53 suction opening, orifice
60 connecting element
61 pierceable membrane, sealing, closure
62 hollow pin
63 filter, filter element
64 recess, groove
65 through hole, small tube
66 second orifice
67 mounting base, base plate
68 funnel, receiving opening
69 piston portion
70 interface element
71 piercing element, opening member
72 cannula, hollow needle
80 bottom plate
81 tongue
82 second reagent reservoir, liquid receiving volume, detection chamber, reagent chamber
83 flow channel
84 detecting chamber 100 container
200 cartridge/base
201 first example of the cartridge
202 second example of the cartridge 300 analysis device
400 sample collecting element
500 cylinder, circumferential wall, cylindrical body
501 closed top end
502 open bottom end
503 handle
600 piston
601 interior cylinder
700 second orifice, puncture opening of the cannula
701 lateral recess, sideward slot
702 rim
703 cylinder
704 receiving groove
800 turbulent flow generating device
801 constriction, acceleration tube
802 second reagent chamber
803 second reagent, magnetic particle reagent
804 magnetic particle
805 outlet
V1 volume of the reagent reservoir
V2 volume for the metered liquid

The invention claimed is:

1. A device for preparing a patient's sample before analysis, comprising:
a housing, wherein the housing comprises a receiving chamber, wherein the receiving chamber is configured to receive a liquid;
an actuator, wherein the actuator is configured to be moved from a first position to a second position, relative to the housing; and
an outflow;
wherein the actuator is configured to extract a first amount of the liquid from the receiving chamber by suction after the actuator enters the second position,
wherein the actuator is configured to prevent extraction of the liquid from the receiving chamber before the actuator enters the second position;
wherein the actuator is configured to supply a second amount of the liquid through the outflow to a reagent chamber, wherein the reagent chamber contains a reagent, such that the reagent is suspended in the second amount of the liquid; and
wherein the actuator comprises a metering chamber, wherein the metering chamber is configured to receive the first amount of the liquid, wherein the metering chamber is configured to supply the second amount of the liquid to the reagent chamber.

2. The device of claim 1, wherein the metering chamber has a first opening and a second opening,
wherein the first opening is configured to draw in the first amount of the liquid,
wherein the second opening is configured to eject the second amount of the liquid through the outflow,
wherein the first opening is different from the second opening.

3. The device of claim 1, wherein the reagent chamber comprises a dry reagent.

4. The device of claim 1, further comprising:
a container, wherein the container comprises the actuator and the housing; and
a base, wherein the base comprises an internal fluidic path, wherein the internal fluidic path comprises an inlet;
wherein the container and the base are provided as separate parts,
wherein the base is configured for interacting engagement with a portion of the container such that the inlet is facing the outflow to form a interfacial path between the base and the container;
wherein the base is further provided with members arranged to open the interfacial path between the actuator and the base when they are functionally engaged with each other;
wherein the base comprises the reagent chamber.

5. The device of claim 4, wherein the base further comprises at least one processing chamber,
wherein the actuator is configured to supply a portion of the liquid to the processing chamber
when the actuator is activated.

6. The device of claim 1, wherein the actuator comprises a metering actuator, wherein the metering actuator is configured to supply at least the first amount of the liquid from the receiving chamber to the metering chamber, wherein the metering chamber provides the first amount of the liquid to the reagent chamber; and
wherein the metering actuator is configured as a sucking actuator configured to suck the first amount of the liquid from the receiving chamber into the metering chamber.

7. The device of claim 1, wherein the actuator comprises a metering actuator, wherein the metering actuator is configured to supply at least the first amount of the liquid from the receiving chamber to the metering chamber, wherein the metering chamber provides the first amount of the liquid to the reagent chamber; and
wherein the metering actuator is configured as a pressing actuator configured to press the second amount of the liquid out of the metering chamber through the outflow to the reagent chamber.

8. The device of claim 1, wherein the actuator comprises a metering actuator, wherein the metering actuator is configured to supply at least the first amount of the liquid from the receiving chamber to the metering chamber, wherein the metering chamber provides the first amount of the liquid to the reagent chamber; and
wherein the metering actuator is configured as both:
a sucking actuator configured to suck the first amount of the liquid from the receiving chamber into the metering chamber; and
a pressing actuator configured to press the second amount of the liquid out of the metering chamber through the outflow to the reagent chamber.

9. The device of claim 8, wherein the metering actuator is provided as a hollow cylinder in which a piston is arranged;
wherein the metering chamber is defined by an inner surface of the cylinder and by the piston,
wherein the cylinder and the piston are configured to be moved in relation to each other to vary a volume of the metering chamber,
wherein, by varying the volume of the metering chamber, a pressure inside of the metering chamber is configured to be increased or decreased.

10. The device of claim 4, wherein the actuator comprises a metering actuator, wherein the metering actuator is configured to supply at least a portion of the liquid from the receiving chamber to the metering chamber, wherein the portion of the liquid provides the first amount of the liquid to the reagent chamber;
wherein the actuator comprises at least one lever member, wherein the at least one lever member is configured to provide a first manually applied activation force to the metering actuator, wherein the at least one lever member is movable in a first direction by placing of the housing onto the base such that the at least one lever member moves relative to the housing due to abutment of the at least one lever member on the base while the base is in interacting engagement with the container, wherein the at least one lever member is configured to provide a second activation force to the metering actuator when a manual force is applied to the at least one lever member, wherein the second activation force is opposite to the first activation force, wherein the at least one lever member is movable in a second direction by moving of the at least one lever member relative to the housing and the base while the housing and the base are engaged with each other.

11. The device of claim 9, wherein the metering chamber comprises a first orifice and a second orifice, wherein the first orifice is configured to extract the first amount of the liquid from the receiving chamber into the metering chamber, wherein the second orifice is configured to supply the second amount of the liquid to the reagent chamber through the outflow.

12. The device of claim 11, wherein the first orifice is provided in the cylinder and the second orifice is provided in the piston.

13. The device of claim 11, wherein the first orifice is arranged in a lower part of the cylinder such that the first orifice provides a connection between the metering chamber and the receiving chamber once the volume of the metering chamber is increased and an underpressure has been built up.

14. The device of claim 11, wherein the second orifice is arranged to be covered with an openable closure that is opened at least partly by an opening member of the base such that the second orifice provides a connection between the metering chamber and the reagent chamber once the first amount of the liquid has been extracted into the metering chamber and the metering actuator is actuated for pressing the second amount of the liquid out of the metering chamber.

15. The device of claim 4, further comprising a seal, wherein the seal is configured to prevent the second amount of the liquid from the metering chamber from entering the reagent chamber; and wherein the base comprises a piercing member protruding from the base such that upon interacting engagement of the base and the container, the piercing member is configured to open the interfacial path by piercing the seal.

16. The device of claim 1, wherein the actuator comprises a metering actuator, wherein the metering actuator is configured to extract the first amount of the liquid from the receiving chamber to the metering chamber, wherein the device further comprises a filtering component, wherein the filtering component is arranged to filter some elements of the first amount of the liquid, wherein the filtering component provides a liquid path between the receiving chamber and the reagent chamber, wherein the metering actuator is arranged such that a transfer of the first amount of the liquid from the receiving chamber flows through the filtering component when the actuator is actuated.

17. The device of claim 1, wherein the actuator is further configured to generate a turbulent flow of the second amount of the liquid through the outflow, when the second amount of the liquid is supplied to the reagent chamber.

18. The device of claim 1, wherein the actuator comprises a supplying actuator configured to supply the reagent from a first reagent supply reservoir to the receiving chamber, so as to combine the reagent with the liquid in the receiving chamber.

19. The device of claim 18, wherein the actuator comprises a second supplying actuator configured to supply a second reagent from a second reagent supply reservoir to the receiving chamber, so as to combine the second reagent with the liquid in the receiving chamber.

20. A system for analyzing a patient's sample, the system comprising:
a sample preparation device for preparing a patient's sample before analysis, comprising:
a housing, wherein the housing comprises a receiving chamber, wherein the receiving chamber is configured to receive the patient's sample;
an actuator, wherein the actuator is configured to be moved from a first position to a second position, relative to the housing; and
an outflow;
wherein the actuator is configured to extract a first amount of the patient's sample from the receiving chamber by suction after the actuator enters the second position,
wherein the actuator is configured to prevent extraction of the patient's sample from the receiving chamber before the actuator enters the second position;
wherein the actuator is configured to supply a second amount of the patient's sample through the outflow to a reagent chamber,
wherein the reagent chamber contains a reagent, such that the reagent is suspended in the second amount of the patient's sample so as to produce a prepared sample; and
wherein the actuator comprises a metering chamber,
wherein the metering chamber is configured to receive the first amount of the patient's sample,
wherein the metering chamber is configured to supply the second amount of the patient's sample to the reagent chamber; and
a sample analysis device configured to conduct at least one analysis of the prepared sample produced by the sample preparation device.

21. A method of preparing a liquid sample before analysis using a sample preparation device, wherein the sample preparation device comprises:
a housing, wherein the housing comprises a receiving chamber, wherein the receiving chamber is configured to receive a liquid sample;
a reagent chamber; and
an actuator configured to transfer a portion of the liquid sample from the receiving chamber to the reagent chamber;
wherein the actuator is configured to be moved from a first position to a second position, relative to the housing, to reduce pressure; and to be moved from the second position to the first position to generate an increased pressure,
wherein the actuator comprises a metering chamber,
wherein the metering chamber is configured to receive a first amount of the liquid sample after the actuator enters the second position, wherein the metering chamber is configured to supply a second amount of the liquid sample to the reagent chamber when the actuator moves toward the first position, the method comprising:
- supplying the liquid sample to the receiving chamber; and
- transferring a portion of the liquid sample from the receiving chamber to the reagent chamber using only two movements of the actuator, comprising:
  - extracting the first amount of the liquid sample from the receiving chamber into the metering chamber by suction by a first movement of the actuator from the first position to the second position;
  - supplying a second amount of the liquid sample from the metering chamber to the reagent chamber by a second movement of the actuator from the second position to the first position; and
  - mixing the second amount of the liquid sample with a reagent in the reagent chamber to produce a prepared sample.

* * * * *